(12) United States Patent
Farrell et al.

(10) Patent No.: US 7,579,373 B2
(45) Date of Patent: Aug. 25, 2009

(54) TARGETED BISPLATINUM POLYAMINES AS PRO-DRUGS: SELECTIVE RELEASE OF PLATINUM

(75) Inventors: Nicholas Farrell, Richmond, VA (US); Alexander Hegmans, Kingston (CA); John D. Roberts, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1084 days.

(21) Appl. No.: 10/225,436

(22) Filed: Aug. 22, 2002

(65) Prior Publication Data

US 2003/0114433 A1    Jun. 19, 2003

(51) Int. Cl.
*A61K 31/27* (2006.01)
*A61K 31/28* (2006.01)
*C07F 15/00* (2006.01)

(52) U.S. Cl. .................. 514/478; 514/483; 514/492; 556/137

(58) Field of Classification Search .......... 514/478, 514/483, 492; 556/137
See application file for complete search history.

(56) References Cited

U.S. PATENT DOCUMENTS

| 4,797,393 A | 1/1989 | Farrell et al. ............. 514/188 |
| 6,022,892 A * | 2/2000 | Farrell et al. ............. 514/492 |

FOREIGN PATENT DOCUMENTS

WO    0109149 A1 *    8/2001

OTHER PUBLICATIONS

Holger Rauter et al. Selective Platination of Biologically Relevant Polyamines, Linear Coordinating Spermidine and Spermine as Amplify Linkers in Dinuclear Platinum Complexes, Inorganic Chemesty 1997, 36, pp. 3919-3927.

* cited by examiner

*Primary Examiner*—Peter G O'Sullivan
(74) *Attorney, Agent, or Firm*—Whitham, Curtis, Christofferson & Cook, P.C.

(57) ABSTRACT

Pro-drug forms of linear polyamine-bridged platinum compounds and methods for their production and use are provided. The polyamine-bridge portion of the compounds is based on spermine or spermidine, and the central amines of the polyamine-bridge are chemically bonded to labile blocking groups. The presence of the blocking groups serves to minimize the toxicity of the Pt compounds upon administration. Selective removal of the blocking groups and release of the active, unblocked species occurs upon exposure to suitable environmental conditions.

61 Claims, 7 Drawing Sheets

TARGETED BISPLATINUM POLYAMINES AS PRO-DRUGS: SELECTIVE RELEASE OF PLATINUM

This invention was made in part using funds from grants from the National Institutes of Health having grant number R01-CA78754. The government may have certain rights in this invention.

DESCRIPTION

BACKGROUND OF THE INVENTION

1. Field of the Invention

The invention generally relates to polyamine-bridged platinum compounds. In particular, the invention provides blocked polyamine-bridged platinum compounds for use as prodrugs.

2. Background of the Invention

Polynuclear platinum complexes represent a discrete class of anticancer agents, distinct in biological activity from the mononuclear cis-DDP (cisplatin) and its congeners (1). Within this class of compounds, a variety of structural types differing in geometry and coordination type is possible (2). FIG. 1 shows the most general structure for these compounds:

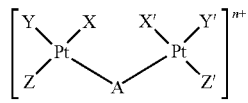

DNA is widely accepted to be the target of platinum-based anticancer agents. The platinum compounds form covalent bonds with DNA, preferably guanine, by displacement of at least one leaving group, usually chloride. FIG. 2 shows the distinct structural types obtainable simply by varying X, Y and Z between Cl and $NH_3$ ligands. The class of most current interest has been the so-called 1,1/t,t series where bifunctional DNA binding is achieved by the displacement of chlorides present in the coordination sphere and trans to the diamine bridge. The general formula for this structural class is shown in FIG. 3 (where Y represents a linear polyamine linker such as a-d of the figure and only the terminal primary amines are bound to the platinum) and may comprise either dinuclear or trinuclear compounds as indicated. The first compound to enter clinical trials from this new structural class is the trinuclear compound designated BBR3464 (FIG. 3b) (3). Polyamine-bridged dinuclear platinum compounds are highly interesting second-generation analogs of BBR3464 because the hydrogen-bonding and electrostatic contributions of the central platinum-amine group in BBR3464 are replicated by the free, non-coordinated "central" quaternary nitrogens of the linear polyamine linker while the presence of two separate Pt—Cl bonds maintains the bifunctional binding mode on the DNA adducts (4). Preclinical investigations confirm the potency of these species with cytotoxicity in the nanomolar range (5).

An interesting feature of the structure-activity relationships within the general structure represented in FIGS. 1 and 3 is that the possibility of hydrogen-bonding and electrostatic interactions in the linker has been shown to greatly enhance the cellular uptake, cytotoxicity and antitumor activity in comparison to a simple diamine linker such as $H_2N(CH_2)_nNH_2$ (e.g. FIG. 3a). In agreement with this observation, all blocked polyamine-bridged compounds are 1-2 orders of magnitude less cytotoxic than their unblocked counterparts (6, 7). Since the only difference is the charge on the compound and the presence of the "central" protonated but non-platinated amine, it is reasonable to assume that these features account for the potent cytotoxicity, i.e. the cytotoxicity and antitumor activity is a function of the specific linking polyamine.

Unfortunately, the remarkable potency of these polyamine-bridged dinuclear platinum complexes results in an extremely narrow therapeutic index. It would be highly desirable to have available forms of polyamine-bridged platinum drugs with enhanced therapeutic indices so that optimal doses could be administered while minimizing toxic side effects. Further, it would be highly desirable to have available forms of these drugs which are capable of targeted or selective release of the highly cytotoxic species.

SUMMARY OF THE INVENTION

It is an object of this invention to provide blocked linear polyamine-bridged platinum compound pro-drugs and methods for their use. The linear polyamine-bridged platinum compounds have the general formula of FIG. 1: [(PtXYZ)-A-(PtX'Y'Z')], where X, Y, Z, X', Y', and Z' are a combination of anionic (usually chloride) and neutral ligands (usually ammonia, $NH_3$) and may be the same or different, and A is a bridging polyamine having a general formula which may be $H_2N(CH_2)_xNBB'(CH_2)_yNH_2$ (where x ranges from about 1 to about 10 and y ranges from about 1 to about 10), or $H_2N(CH_2)_xNBB'(CH_2)_yNBB'(CH_2)_xNH_2$ (where x ranges from about 1 to about 10 and y ranges from about 1 to about 10):

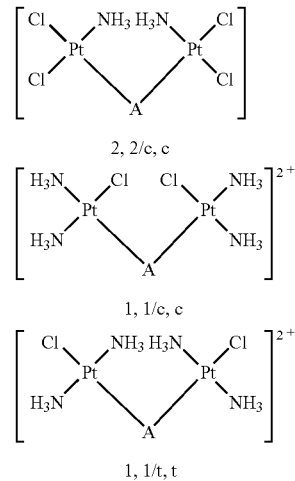

Further, B and B' are hydrogen or a labile blocking group which may be the same or different, and may be the same or different at each location within the molecule, (e.g. in the case where two amines are present in the bridging polyamine) and at least one central amine of the bridging polyamine portion is blocked with a labile blocking group such as carbamate or amide. Further, B' may be present or absent, depending on the pH of the medium. The anionic groups may be halide, pseudohalide, substituted pseudohalide, sulphate, phosphate, phosphonate, nitrate, carboxylate, substituted carboxylate, dicarboxylate, and substituted dicarboxylate; the neutral group may be substituted or unsubstituted and is selected from the group consisting of ammonia, a primary or secondary amine, a "dangling" diamine $H_2N(CH_2)NBB'$ where only the —NH$_2$ moiety is bound to the platinum, sulfoxide, phosphine, pyridine, substituted pyridine, quinoline, imidazole, thiazole, pyrimidine, purine, acridine, pyrazole, benzimidazole, or benzothiazole. In a preferred embodiment, the anion is chloride and the neutral group is ammonia, NH$_3$. Further, in the 1,1/c,c configuration, Y, Y', Z and Z' may be chelating bidentate diamines (such as ethylenediamine, propylenediamine, 1,2-diaminocyclohexane, or 1,1-diaminomethylcyclohexane).

The bridging polyamine portion of the compound may be H$_2$N(CH$_2$)$_x$NBB'(CH$_2$)$_y$NH$_2$ where x ranges from about 1 to about 10 and y ranges from about 1 to about 10. In some embodiments: x=4 and y=3; or x=6 and y=6; or x=7 and y=8. Alternatively, the bridging polyamine portion of the compound may be H$_2$N(CH$_2$)$_x$NBB'(CH$_2$)$_y$NBB'(CH$_2$)$_x$NH$_2$ where x ranges from about 1 to about 10 and y ranges from about 1 to about 10. In some embodiments: x=4 and y=3; or x=6 and y=2; or x=5 and y=4.

The labile blocking group may be selected from carbamate protection group residues such as t-butyl (tBOC), benzyl (CBz), fluorenylmethyl (Fmoc), adamantyl (1-Adoc), piperidinyl (Pipoc), allyl, vinyl; and amide protection groups derived from carboxylates such as acetyl, trifluoroacetyl, monochloroacetyl, and 2-(benzoyloxymethyl)benzoyl (BOMB), and may further comprise a targeting group.

The invention further provides a method for the provision of a linear polyamine-bridged platinum compound, comprising the steps of positioning a blocked linear polyamine-bridged platinum compound formed by attaching a labile blocking group to at least one central amine function of a bridging polyamine portion of the compound at the location of interest and 2) exposing the blocked linear polyamine-bridged platinum compound to an environmental stimulus which causes removal of the labile blocking group.

The blocked linear polyamine-bridged platinum compound has the general formula [(PtXYZ)-A-(Pt X'Y'Z')], where X, Y, Z, X', Y', and Z' are a combination of anionic (usually chloride) and neutral ligands (usually ammonia, NH$_3$), and A is a bridging polyamine having a general formula which may be H$_2$N(CH$_2$)$_x$NBB'(CH$_2$)$_y$NH$_2$ (where x ranges from about 1 to about 10 and y ranges from about 1 to about 10), or H$_2$N(CH$_2$)$_x$NBB'(CH$_2$)$_y$NBB'(CH$_2$)$_x$NH$_2$ (where x ranges from about 1 to about 10 and y ranges from about 1 to about 10). B and B' are hydrogen or a labile blocking group such as a carbamate or amide and may be the same or different, and at least one central amine of the bridging polyamine portion is blocked with a labile blocking group. Further, B' may be present or absent, depending on the pH of the medium.

The anionic groups may be halide, pseudohalide, substituted pseudohalide, sulphate, phosphate, phosphonate, nitrate, carboxylate, substituted carboxylate, dicarboxylate, and substituted dicarboxylat. Neutral groups may be substituted or unsubistituted and may be ammonia, a primary or secondary amine, a "dangling" diamine H$_2$N(CH$_2$)NBB' where only the —NH$_2$ moiety is bound to the platinum, sulfoxide, phosphine, pyridine, substituted pyridine, quinoline, imidazole, thiazole, pyrimidine, purine, acridine, pyrazole, benzimidazole, or benzothiazole. Further, in the 1,1c/c,c configuration, Y, Y', Z and Z' may be chelating bidentate diamines (such as ethylenediamine, propylenediamine, 1,2-diaminocyclohexane, or 1,1-diaminomethylcyclohexane).

The bridging polyamine portion of said compound may be H$_2$N(CH$_2$)$_x$NBB'(CH$_2$)$_y$NH$_2$ where x ranges from about 1 to about 10 and y ranges from about 1 to about 10. In some embodiments: x=4 and y=3; or x=6 and y=6; or x=7 and y=8. Alternatively, the bridging polyamine portion of said compound may be H$_2$N(CH$_2$)$_x$NBB'(CH$_2$)$_y$NBB'(CH$_2$)$_x$NH$_2$ where x ranges from about 1 to about 10 and y ranges from about 1 to about 10. In some embodiments: x=4 and y=3; or x=6 and y=2; or x=5 and y=4.

The labile blocking group may be selected from carbamate protection group residues such as t-butyl (tBOC), benzyl (CBz), fluorenylmethyl (Fmoc), adamantyl (1-Adoc), piperidinyl (Pipoc), allyl, vinyl; amide protection groups derived from carboxylates such as acetyl, trifluoroacetyl, monochloroacetyl, 2-(benzoyloxymethyl)benzoyl (BOMB), and the blocking group may further comprises a targeting element.

The environmental stimulus may be, for example, pH or an enzyme.

The invention also provides a method for killing cancer cells, comprising the step of providing to the cancer cells a linear polyamine-bridged platinum compound having the general formula [(PtXYZ)-A-(Pt X'Y'Z')], where X, Y, Z, X', Y', and Z' where X, Y, Z, X', Y', and Z' are a combination of anionic (usually chloride) and neutral ligands (usually ammonia, NH$_3$). A is a bridging polyamine having a general formula which may be H$_2$N(CH$_2$)$_x$NH$_2$(CH$_2$)$_y$NH$_2$ (where x ranges from about 1 to about 10 and y ranges from about 1 to about 10), or H$_2$N(CH$_2$)$_x$NH$_2$(CH$_2$)$_y$NH$_2$(CH$_2$)$_x$NH$_2$ where x ranges from about 1 to about 10 and y ranges from about 1 to about 10. At least one central amine function of the bridging polyamine portion is blocked with a labile blocking group such as a carbamate or amide. The linear polyamine-bridged platinum compound is provided in a quantity sufficient to kill the cancer cells.

The anionic groups may be halide, pseudohalide, substituted pseudohalide, sulphate, phosphate, phosphonate, nitrate, carboxylate, substituted carboxylate, dicarboxylate, and substituted dicarboxylate. The neutral group may be substituted or unsubistituted and may be ammonia, a primary or secondary amine, a "dangling" diamine H$_2$N(CH$_2$)NBB' where only the —NH$_2$ moiety is bound to the platinum, sulfoxide, phosphine, pyridine, substituted pyridine, quinoline, imidazole, thiazole, pyrimidine, purine, acridine, pyrazole, benzimidazole, or benzothiazole. Further, in the 1,1/c,c configuration, Y, Y', Z and Z' may be chelating bidentate diamines (such as ethylenediamine, propylenediamine, 1,2-diaminocyclohexane, or 1,1-diaminomethylcyclohexane).

The bridging polyamine portion of the compound may be H$_2$N(CH$_2$)$_x$NBB'(CH$_2$)$_y$NH$_2$ where x ranges from about 1 to about 10 and y ranges from about 1 to about 10. In some embodiments: x=4 and y=3; or x=6 and y=6; or x=7 and y=8. Alternatively, the bridging polyamine portion may be H$_2$N(CH$_2$)$_x$NBB'(CH$_2$)$_y$NBB'(CH$_2$)$_x$NH$_2$ where x ranges from about 1 to about 10 and y ranges from about 1 to about 10. In some embodiments: x=4 and y=3; or x=6 and y=2; or x=5 and y=4.

The labile blocking group may be selected from carbamate protection group residues such as t-butyl (tBOC), benzyl (CBz), fluorenylmethyl (Fmoc), adamantyl (1-Adoc), piperidinyl (Pipoc), allyl, vinyl; amide protection groups derived from carboxylates such as acetyl, trifluoroacetyl, monochloroacetyl, 2-(benzoyloxymethyl)benzoyl (BOMB), and may further comprise a targeting element. The environmental stimulus may be, for example, pH or an enzyme.

The invention further provides a method of producing a linear platinum compound with a polyamine bridge in which amine groups of the polyamine bridge are blocked with an amide blocking group. The method includes the steps of 1) substituting anionic leaving groups of the linear platinum compound with acetate to form an acetate derivative of the linear platinum compound; 2) blocking amine groups of the polyamine bridge by reacting the acetate derivative of the linear platinum compound with an acid anhydride of the proposed amide blocking group under anhydrous conditions to form a blocked acetate derivative of the linear platinum compound; and 3) forming a blocked anionic derivative of the linear platinum compound by exposing the blocked acetate derivative of the linear platinum compound to anions under conditions which result in the replacement of the platinum-bound acetate by anionic groups.

The invention further provides a method of producing a linear platinum compound with a polyamine bridge in which amine groups of said polyamine bridge are blocked with a carbamate blocking group. The method comprises the step of reacting the linear platinum compound with a carbamate precursor in an alkaline dioxane/water system under conditions in which a blocked carbamate derivative of the linear platinum compound is formed. By "carbamate precursor" we mean for example, the standard use of Di-tert-butyldicarbonate (t-BOC)$_2$O or fluorenylmethylchloroformate (Fmoc-Cl) which produce the t-Boc and Fmoc blocked groups, respectively (See green, T. W. and Wuts, P. G. M. *Protective Groups in Organic Chemistry*, John Wiley & Sons, 3$^{rd}$ ed., (1999), and references cited therein).

DETAILED DESCRIPTION OF THE PREFERRED EMBODIMENTS OF THE INVENTION

The present invention provides blocked pro-drug forms of linear polyamine-bridged platinum compounds and methods for their production and use. The pro-drug forms display enhanced therapeutic indices due to decreased toxicity and selective release of the toxic component.

Figure 2:
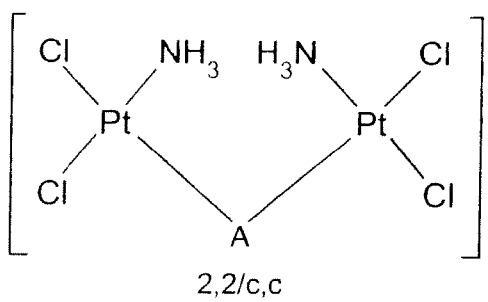
FIG. 2 shows specific examples of different structural classes obtained by systematic variation of X,Y,Z and X',Y',Z' of FIG. 1. The abbreviations refer to the number of leaving groups and the configuration of each Pt center, e.g. 1,1/t,t refers to the presence of one leaving group (Cl) on each platinum and trans to the linker chain.
Figure 2:
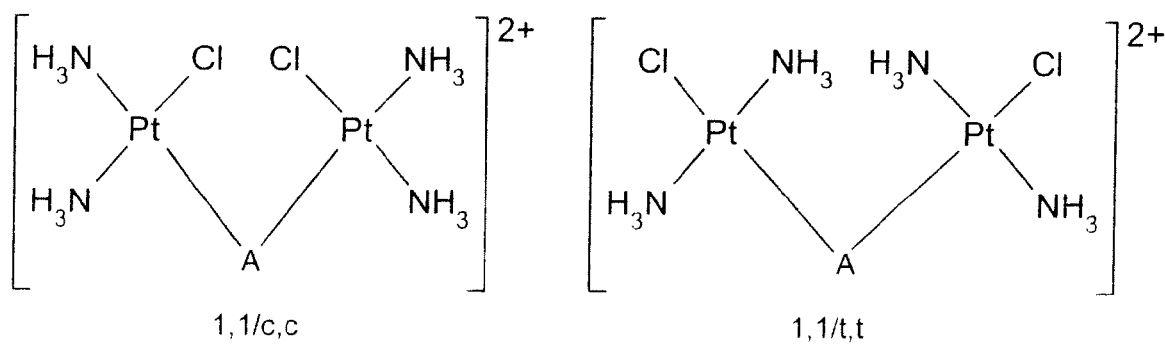
Figure 3A:
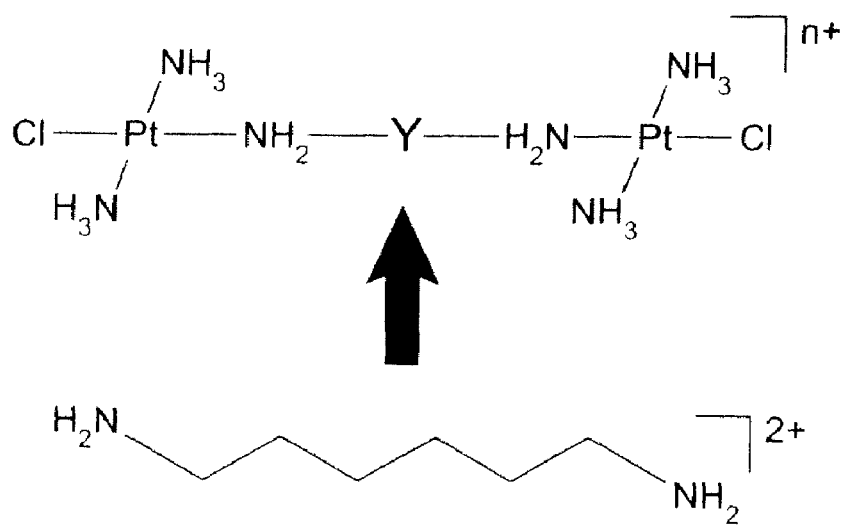
FIG. 3 shows the general structure of di and trinuclear linear Pt polyamine compounds: a) 1,1/tt; b) 1,0,1/ttt (BBR3464; c) 1,1/tt-spermine; d) 1,1/tt-spermidine The linear diamine depicted in (a) can be used as a control compound.
Figure 3B:
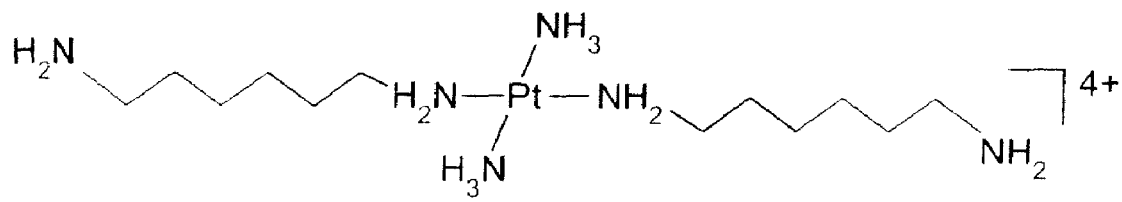
Figure 3C:
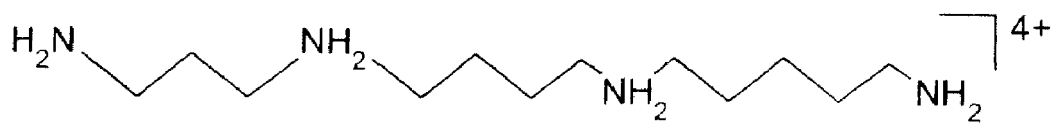
Figure 3D:
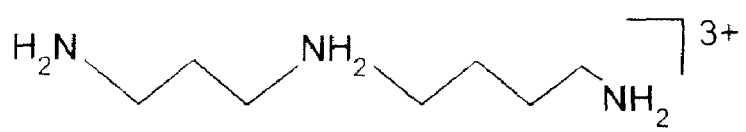
Figure 4:
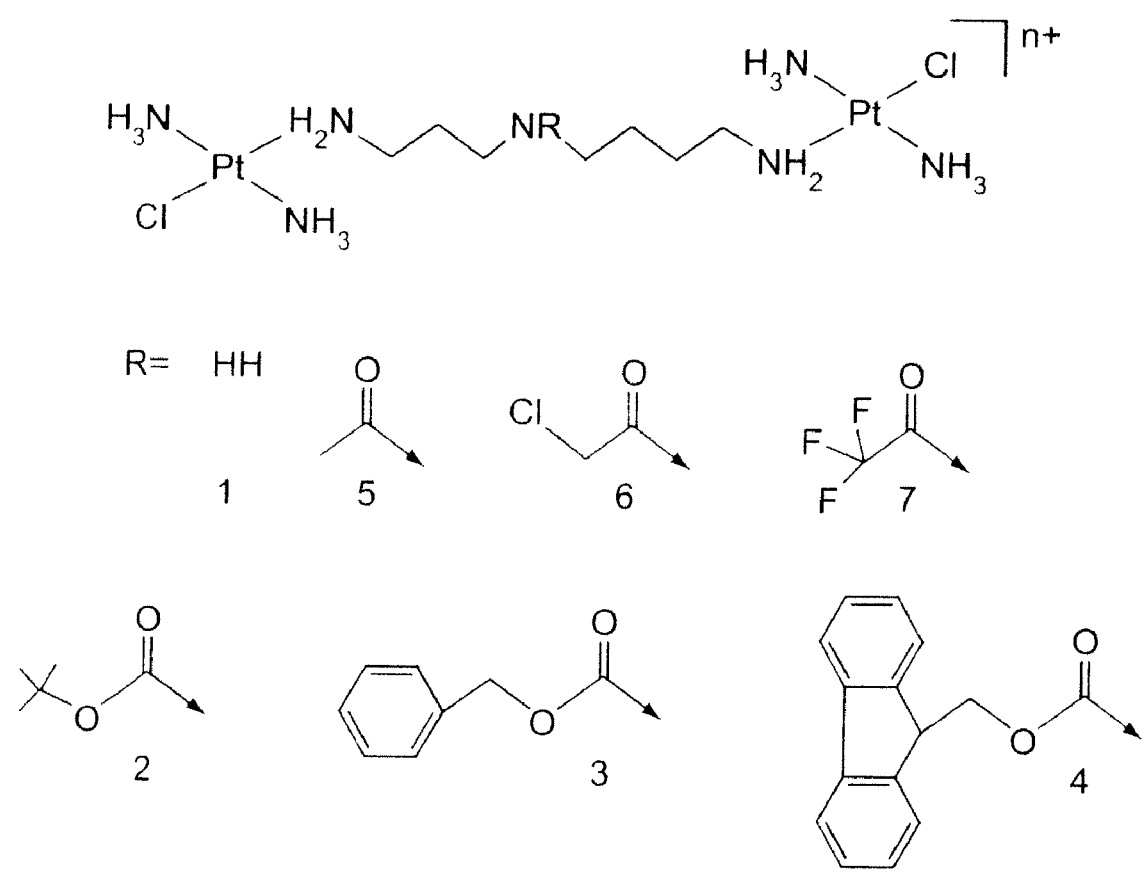
FIG. 4. Chemical structures of the dinuclear platinum complexes 1-7 (1: n=3; 2-7: n=2).

By "linear polyamine-bridged platinum complexes" we mean platinum compounds of the general formula [(PtXYZ)-A-(Pt X'Y'Z')], where X, Y, Z, X', Y', and Z'may be the same or different and are a combination of anionic and neutral ligands. FIG. 2 shows exemplary structural classes obtainable by varying X, Y, Z, X', Y', and Z' between Cl and NH$_3$ ligands. The classes include: the 1,1/t,t series where one chloride is present in each coordination sphere trans to the diamine bridge; the 1,1/c,c series where one chloride is present in each coordination sphere cis to the diamine bridge; and the 2,2/c,c series where two chlorides are present in each coordination sphere. For 2,2 compounds the cis/trans distinction refers to the mutual positions of the two chloride groups.

Examples of suitable anionic groups include halide (including chlorine, bromine, iodine and fluorine), pseudohalide, substituted pseudohalide, sulphate, phosphate, phosphonate, nitrate, carboxylate, substituted carboxylate, dicarboxylate, and substituted dicarboxylate. Examples of suitable neutral groups (which may be substituted or unsubsititute) include primary or secondary amines, a "dangling" diamine H$_2$N(CH$_2$)NBB' where only the —NH$_2$ moiety is bound to the platinum, sulfoxide (e.g. DMSO) or phosphine, pyridine, or planar aromatic or pseudo-aromatic pyridine-like ligands such as substituted pyridine, quinoline, imidazole, thiazole, pyrimidine, purine acridine, pyrazole, benzimidazole, benzothiazole and the like; and A is a bridging polyamine in which one or more of the "central" non-platinated amines is "blocked" (see below).

The sulfoxide preferably has the formula R$_2$SO where each R is a straight chain or branched alkyl group having one to 12 carbon atoms. The sulfoxide substituent may optionally be substituted preferably with an aromatic, e.g. aryl or alkaryl, group.

The amines may be aliphatic or aromatic and generally include ammonia, branched or straight chain lower alkyl amine, aryl amines, aralkyl amines, lower alkenyl amines, cycloalkyl amines, cycloalkenyl amines, and polycyclic hydrocarbon amines.

Substituted or unsubstituted heterocyclic amines, nucleosides, nucleotides, pyridine-type nitrogen containing compounds, and the like may be used in the practice of the present invention. Suitable substitutents include but are not limited to alkyl, aromatic aryl, hydroxy, lower alkoxy, carboxylic acid or acid ester, nitro- and halogen substituents.

Purines and pyrimidines which are suitable in the practice of the present invention include, for example, cytosine, uracil, thymine, guanine, adenine, xanthine, hypoxanthine, purine, pyrimidine and their substituted derivatives.

Where the anionic group is a carboxylate or a substituted carboxylate, the anionic group may be represented by the formula:

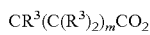

$$CR^3(C(R^3)_2)_mCO_2$$

wherein m is an integer from 0 to 5, inclusive. The R$^3$ groups may be the same or different and may be hydrogen, substituted or unsubstituted straight or branched chain alkyl, aryl, alkaryl, alkenyl, cycloalkyl, cycloalkenyl, halogen, pseudohalogen, hydroxy, carbonyl, formyl, nitro, amido, amino, alkoxy, aryloxy, sulphonic acid salt, carboxylic acid ester or carboxylic acid salt. Furthermore, the R$^3$ groups can be combined so that two R$^3$ groups represent a double bond oxygen or sulphur atom.

Lower alkyl and lower alkenyl in the present specification means one to five carbon atoms. Unless indicated otherwise, alkyl or alkenyl means 1 to 12 carbon atoms. By cycloalkyl is meant chains of 3 to 10 carbon atoms. Substituted in the present specification, unless indicated otherwise, is intended to mean substitution with a group chosen from alkyl, aryl, cycloalkyl of 3 to 10 carbon atoms, cycloalkenyl, aralkyl, halogen, pseudohalogen, hydroxy, alkoxy, cycloamino, or carboxylic acid salts or esters of one to ten carbon atoms.

The term pseudohalide in the present invention has the following meaning: a molecule consisting of more than two electronegative atoms which, in the free state, represent halogen atoms (see page 560 of "Advanced Inorganic Chemistry" by Cotton and Wilkinson, Interscience Publishers, 1966). Examples of these molecules include carboxylate, cyanide, cyanate, thiocyanate, and azide.

Preferably, there are one or two chloride ions on each Pt atom; thus, a total of two to four chloride ions are present on the preferred compounds of the present invention.

The bridging polyamine portion of the molecule is of the general formula $H_2N(CH_2)_xNBB'(CH_2)_yNH_2$ or $H_2N(CH_2)_xNBB'(CH_2)_yNBB'(CH_2)_xNH_2$ where x is generally in the range of about 1 to about 10, and Y is generally in the range of about 1 to about 10. In one embodiment of the invention, the bridging polyamine portion of the molecule is $H_2N(CH_2)_xNBB'(CH_2)_yNH_2$ and x=4 and y=3 (i.e. the bridging polyamine is spermidine), or x=4 and y=3; or x=6 and y=6; or x=7 and y=8. In another embodiment of the invention, the bridging polyamine is $H_2N(CH_2)_xNBB'(CH_2)_yNBB'(CH_2)_xNH_2$ and x=4 and y=3 (i.e. the bridging polyamine is spermine) or x=4 and y=3; or x=6 and y=2; or x=5 and y=4.

By a "blocked pro-drug form" we mean a form of the linear polyamine-bridged Pt compound in which one or more of the "central" non-platinated amines located within the polyamine bridging portion of the molecule is chemically bonded to a moiety other than hydrogen. Further, the moiety is labile in that it can be attached to and removed from the amine(s) under conditions that do not destroy the integrity of the linear polyamine-bridged platinum compound. The chemistry of amine groups is well-understood and those of skill in the art will recognize that many methods are available for effecting their modification. For example, see Green, T. W. and Wuts, P. G. M. *Protective Groups in Organic Chemistry*, John Wiley & Sons, 3$^{rd}$ ed., (1999), and references cited therein. It will be appreciated that for carbamates and amides the central nitrogen carrying the B (blocking group) is not protonated (i.e. B' is not present) but in other cases such as N-alkyl or N-aryl amine blocking groups, the nitrogen may be protonated depending on the pH of the medium (i.e. B' is present and is H). Further, those of skill in the art will recognize that, when multiple amine groups are present in a compound, some of the amines may possess a B blocking group and B' may be absent at that particular blocked amine, whereas other amine groups may possess B=B'=hydrogen. In other words, some amine groups may be left unblocked, while others are protected.

The purpose of the introduction of the blocking groups is to attenuate the activity, potency and/or toxicity of the compound until exposure to a desired environmental trigger, stimulus, location, etc., is achieved. The therapeutic index of the Pt drug is thus increased. For example, a Pt compound that is highly toxic to cells and which induces noxious side effects may be rendered relatively innocuous or inactive by the presence of blocking groups until the blocked pro-drug encounters an environment in which the pH is favorable for hydrolysis and removal of the blocking groups. Alternatively, the blocking groups may be susceptible to removal by enzymatic cleavage. The pro-drug form of the compound would then be stable until exposure to the enzyme, for example, within a particular type of cell (e.g. a cancer cell) known to produce or overproduce the enzyme, by natural or engineered methods.

Further, certain blocking groups may also function to direct the pro-drug compound to a particular location where removal of the blocking groups, and release of the active species, occurs. For example, certain blocking groups may, by virtue of their general properties (e.g. charge, hydrophilicity, etc.) predispose the pro-drug to, e.g. cross the cell membrane, or alternatively, to remain outside the cell.

Further, the blocking groups may also be or comprise targeting elements which serve to specifically direct the pro-drug to a desired site within the body. For example, the blocking group may include a peptide targeting sequence to target the pro-drug to a particular cell type, or to a particular location within a cell. Alternatively, antibodies specific for a particular antigen are known which can direct an attached moiety (e.g. the platinum compound) to a particular cell type which displays such antigens. Such specific targeting elements may be in entirety, comprise part of, or otherwise be associated with the blocking groups.

Alternatively, in some cases it may be desirable to simply attach a blocking group that is slowly removed (e.g. hydrolyzed) from the pro-drug while the pro-drug remains at or near the site of administration (e.g. upon direct injection into a tumor); or which upon administration is non-specifically distributed (for example, via the digestive or circulatory system) in order to provide a sustained "timed-release" of the active species throughout the system.

Those of skill in the art will recognize that a wide range of potential blocking groups exist which may be utilized to block polyamine-bridged platinum compounds. Examples, of such blocking groups include but are not limited to carbamate protection group residues such as t-butyl (tBOC), benzyl (CBz), fluorenylmethyl (Fmoc), adamantyl (1-Adoc), piperidinyl (Pipoc), allyl, vinyl; amide protection groups such as acetyl, trifluoroacetyl, monochloroacetyl, 2-(benzoyloxymethyl)benzoyl (BOMB). Further, a polyamine-bridged platinum compound with multiple central amines such as spermine may be blocked with a single type of blocking group, or with more than one type. In addition, as described above, the blocking groups may also contain other moieties (such as general or specific targeting elements) that serve to aid their uptake and/or retention in a desired location.

The choice of a particular blocking group will be predicated on a number of different factors, such as ease of reactivity with the Pt compound. Such factors may be taken into account when designing the pro-drugs in order to give the pro-drug desired properties which influence their selectivity and biological activity. For example, carbamates are known to differ in acid susceptibility and the choice of which to utilize may be based on, e.g., the desired route of administration. For example, the stability of the FMOC complex at pH 5 and 6 could allow for oral delivery of the pro-drug, stabilizing the compound to the acid of the stomach but ultimately releasing the active species at pH 7-8 upon injection.

Figure 5:
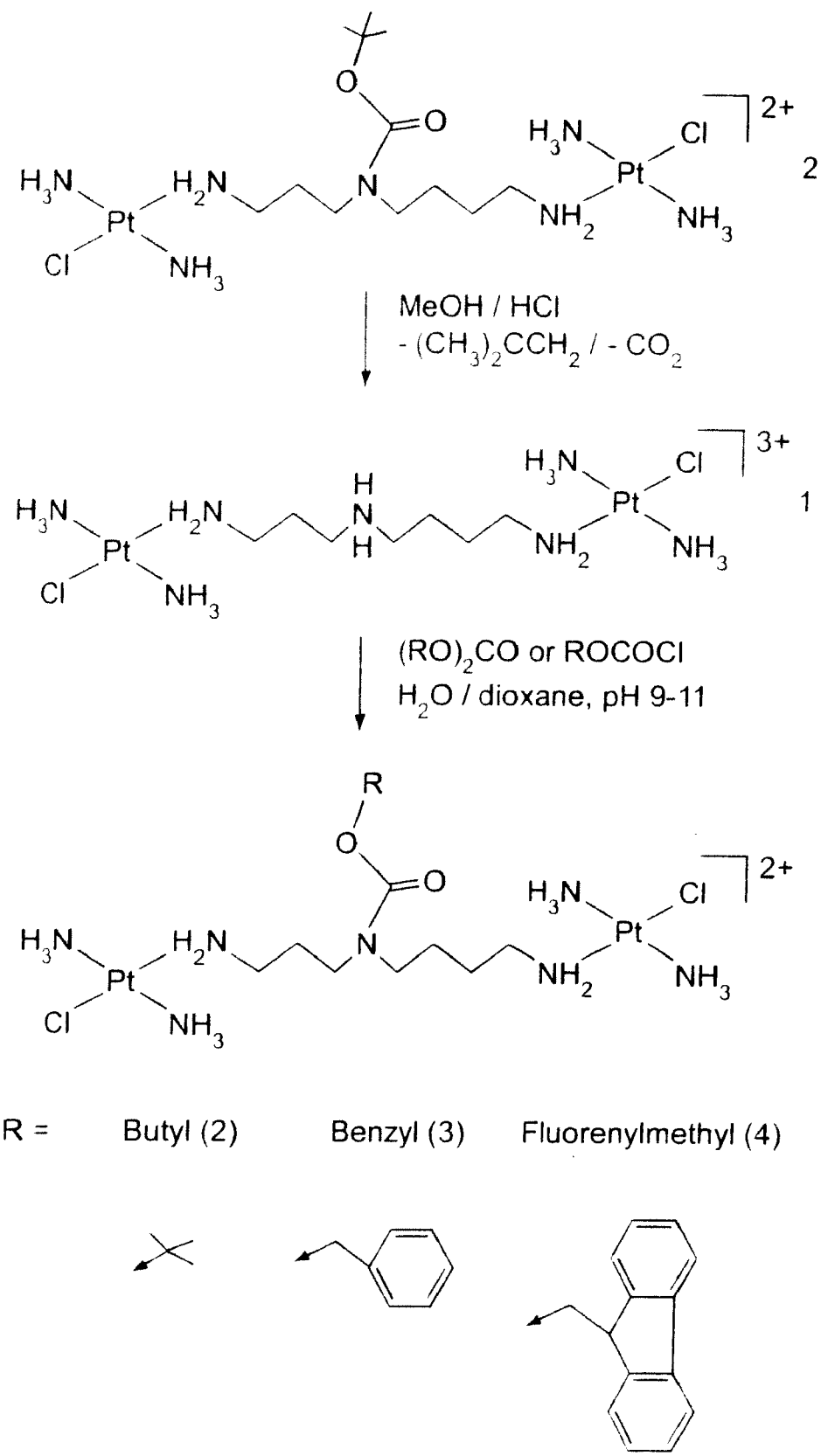
FIG. 5. Synthesis scheme for compounds 1-4. Complex 1 is prepared from 2 by acidic hydrolysis of the BOC protection group. Reintroduction of a blocking group leads to the formation of the various protected amines 2-4.
Figure 6:
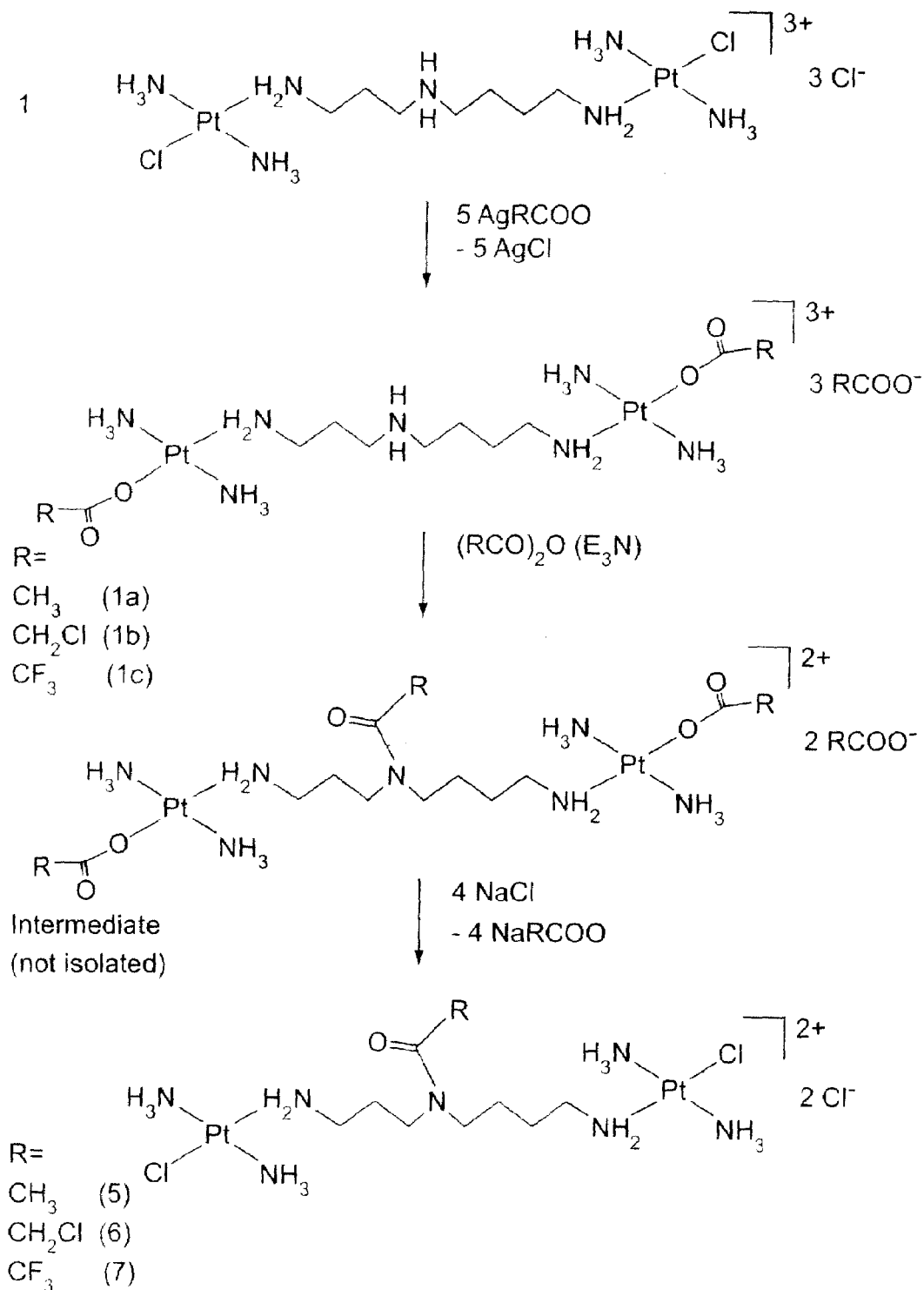
FIG. 6. Schematic of the pathway for the synthesis of the amide-protected platinum spermidine complexes 5-7.

The chemistry of amine groups is well-understood and those of skill in the art will recognize that many methods are available for effecting their modification. For example, see Green, T. W. and Wuts, P. G. M. *Protective Groups in Organic Chemistry*, John Wiley & Sons, 3$^{rd}$ ed., (1999), and references cited therein. However, in order to introduce a blocking group as described herein, some special considerations must be taken into account. For example, see Hegmans, A., Qu, Y., Kelland, L. R., Roberts, J. D. and Farrell, N. "Novel Approaches to Polynuclear Platinum Pro-Drugs. Selective Release of Cytotoxic Platinum-Spermidine Species through Hydrolytic Cleavage of Carbamates" *Inorg. Chem.* 40:6108-6114(2001). In one embodiment of the present invention, the blocking groups are carbamate-type groups. The introduction of such groups into a linear platinum compound may be accomplished by a synthesis scheme such as that depicted in FIG. 5. However, those of skill in the art will recognize that other alternative synthesis protocols exist which can be used with equal or similar efficacy. Examples include but are not limited to synthesis and design of a suitable polyamine prior to incorporation into the dinuclear platinum moiety whereas the innovation described herein affords a blocked species from the intact pre-formed polyamine-platinum compound. Further, for other types of blocking groups, alternative synthesis schemes will be appropriate. For amides, a general scheme may involve conversion of 1 to a acetate or substituted acetate derivative and subsequent reaction with acid anhydrides, followed by reaction with aqueous NaCl, as described in Example 4 below (See also FIG. 6). Any suitable synthesis scheme, many of which are known to those of skill in the art, may be utilized to produce the blocked linear platinum compounds of the present invention.

The pro-drugs of the present invention may be administered by any of a wide variety of means which are well known to those of skill in the art, (including but not limited to intravenously, intramuscularly, intraperitoneallly, orally, rectally, intraocularly, and the like) and may be in any form (e.g. liquid, solid, etc.) which is suitable for the means of administration. Further, the pro-drugs may be administered together with other agents in a treatment protocol, e.g. with or in conjunction with radiation, other chemotherapeutic agents, vitamins, substances for control of nausea or pain, etc. In addition, they may be administered in a form which ensures the release of the active Pt species such as with another compound which generates the stimulus for removal of the blocking groups, for example, another compound which causes a change in pH in the local environment of the pro-drug.

In a preferred embodiment of the present invention, the blocked pro-drug forms of linear polyamine-bridged platinum compounds of the present invention are used to treat cancer. Those of skill in the art will recognize that many types of cancer are known to respond to Pt drugs in general, and the blocked compounds of the present invention may be utilized to treat any of these, examples of which include but are not limited to solid tumors of any type, (e.g. ovarian cancer, prostate cancer, and the like).

The present invention also provides a method for providing a linear polyamine-bridged platinum compound at a location of interest. A location of interest may be within a patient (e.g. at the site of a tumor). Alternatively, the location may be en ex vivo location, or a location where the provision of a linear polyamine-bridged platinum compound is desired in an application such as for use in a diagnostic method, in a laboratory technique, etc. The method involves positioning a blocked linear polyamine-bridged platinum compound (which is formed by attaching a labile blocking group to at least one central amine function of the bridging polyamine portion of the compound) at the location of interest. This is followed by exposing the blocked linear polyamine-bridged platinum compound to an environmental stimulus which causes removal of the labile blocking group. Positioning of the blocked linear polyamine-bridged platinum compound may be accomplished by any of several means known to those of skill in the art which would be suitable for the desired application. For example, in the treatment of disease (e.g. cancer as discussed above) positioning of the blocked compound may be effected by, for example, IV administration, injection, oral ingestion, etc. Alternatively, positioning may be accomplished by, for example, attaching the blocked compound to a matrix and situating the matrix at the location of interest, which may be within a patient, or within a vessel suitable for other applications such as diagnostic or laboratory techniques.

EXAMPLES

Methods

Starting Materials. [{trans-Pt(NH$_3$)$_2$Cl}$_2$-μ-spermidine-N$^1$,N$^8$]Cl$_3$ (1) was prepared according to the published method (6). Briefly, a selectively blocked polyamine with the central nitrogens containing the N-BOC group is prepared. Then upon platination and production of the linear blocked polyamine-bridged platinum compound, the BOC group is removed by mild acid giving the polyamine-bridged compound with the protonated "central" amines (6). Di-tert-butyldicarbonate, benzylchloroformate and fluorenylmethylchloroformate were purchased from Aldrich and used without further purification. Silver acetate, silver trifluoroacetate, acetic anhydride and chloroacetic anhydride were purchased from Aldrich, trifluoroacetic anhydride was purchased from Fluka. Silver chloroacetate was obtained by dissolving Ag$_2$O in an aqueous solution of chloroacetic acid (Aldrich).

Instrumentation. $^1$H NMR spectra were measured in D$_2$O solution on a Varian Mercury 300 MHz spectrometer using sodium(trimethylsilyl)propionsulfonate (TSP, δ=0.00 ppm relative to TMS) as internal reference. $^{195}$Pt spectra were recorded in D$_2$O at 64 MHz using K$_2$[PtCl$_6$] as external reference.

IR spectra were measured as KBr pellets on a Nicolet Nexus 670 FT-IR instrument. Elemental analyses were performed by Quantitative Technologies Inc., Whitehouse, N.J.

pH measurements were taken on a Corning 340 pH meter with combined glass electrode. pD values in deuterated solutions were obtained by addition of 0.4 units to the meter reading. Extinction coefficients were determined with a Jasco V-550 UV/VIS spectrophotometer using 1 cm cuvettes.

Analyses of the products and hydrolysis studies were carried out on an analytical Beckman System Gold Nouveau HPLC instrument with UV detection at 215 nm. A Lichrosphere RP-8 column (5 μm particle size, dimensions 250 mm×4 mm) was used with a solvent gradient from water/methanol 97:3 (0.05 M NaClO$_4$, 1% NaCl) to water/methanol 70:30 (0.05 M NaClO$_4$, 2% NaCl).

Hydrolysis Study. For the hydrolysis experiments 10$^{-3}$ mMol complex were dissolved in 1 mL of nanopure water. The pH of the solutions was adjusted by addition of HNO$_3$ (0.1 M, 0.01 M) and NaOH (0.1 M, 0.01 M), respectively. The samples were incubated in a water bath at 37° C. and aliquots of 20 μL were taken from the bulk solution for HPLC analysis. The pH values of the samples were controlled in regular intervals and readjusted if necessary.

Biological Assays

Cell culture. A2780, A2780/CDDP, CH1, CH1/CDDP, 41M and 41M/CDDP cell lines were used in this study and maintained according to published procedures. (8,9).

Growth inhibition assay. The Sulforhodamine B (SRB) assay was used to determine growth inhibition potency of platinum drugs (10). The cells were seeded in 96-well microtitre plates at 3-8×10$^3$ cells/well in 160 μL growth medium and allowed to attach overnight. Platinum agents were then added after serial dilution in quadruplicate wells and exposed to cells for 2 or 96 hours. After the 2 hours drug incubations were complete, plates were washed free of drug with phosphate-buffered saline (PBS) and then refed with normal growth medium for a further 94 hours. Quantitation of cell growth in treated and control wells was then assessed using 0.4% SRB dissolved in 1% acetic acid. IC$_{50}$ values were determined graphically.

Cellular accumulation. The cellular accumulation assays followed published procedures (7). Briefly, cells were resuspended at 10$^7$/mL in media supplemented with 25 μM HEPES. Platinum complexes were added, and samples were incubated at 37° C. in 5% CO$_2$. At 0 and 2 hours aliquots were removed for determination of cell concentrations and for measurement of platinum content. For the latter, aliquots were washed three times in cold phosphate buffered saline, resuspended in 1% Triton-X in water, and sonicated. Platinum content was measured by flameless atomic absorption spectroscopy.

Example 1

Acidity of the N4 Position of Platinum-bound Spermidine

In order to find the optimal conditions for the synthetic procedure, the $pK_a$ of the N4 site of the unprotected Pt spermidine complex 1 was determined prior to the protection reactions (6). A pH titration was carried out and monitored by $^1$H NMR spectroscopy (11 and 12). The obtained $pK_a$ value of 9.24±0.05 is significantly lower compared to values of various secondary aliphatic amines which range from 10.5-11.0 (13). The increased acidity is most likely a consequence of the electron withdrawing effect of the coordinated platinum centers.

Example 2

Synthesis and Characterization of Compounds 2-4

The synthesis of the carbamate-blocked spermidine compounds was achieved in a water/dioxane mixture at pH values between 9-11. These conditions provided a sufficient percentage of the deprotonated amine which reacted as a nucleophile during the protection step. The compounds were isolated as chloride salts and were characterized by HPLC and $^1$H NMR spectroscopy. The BOC-protected Pt spermidine complex was synthesized earlier as an intermediate during the preparation of 1, and characterized as a mixed chloride/nitrate salt (6). Compound 2 shows an identical HPLC profile and $^1$H NMR spectrum as the precursor compound of 1, confirming that the BOC protection group could be reintroduced to the N4 position via the described pathway (FIG. 2). The synthetic procedure was then used to obtain a series of carbamates which varied only in the aliphatic or aromatic residue on the protection group.

Preparations. [{trans-Pt(NH$_3$)$_2$Cl}$_2$——N$^4$-BOC-spermidine-N$^1$,N$^8$]Cl$_2$ (2). To a solution of 0.1 mMol 1 in 7 mL H$_2$O is added 0.25 mMol di-tert-butyldicarbonate in 3 mL dioxane. 1 M NaOH is added drop wise to reach pH 10-11. The solution is stirred for 24 h at ambient temperature, the pH is readjusted to 10 approximately 3 h after the start of the reaction. The clear solution is then evaporated to dryness, the remaining colorless residue is redissolved in 40 mL of methanol. The insoluble starting compound is removed by filtration, and the filtrate is concentrated by rotary evaporation until a precipitate forms. 5 mMol LiCl dissolved in methanol are added and the mixture is cooled to 4° C. over night. The colorless product is collected by filtration in 62% yield. Anal. Calcd for $C_{12}H_{39}N_7O_2Cl_4Pt_2$: C, 17.05; H, 4.65; N, 11.60; Cl, 16.77. Found: C, 16.79; H, 4.63; N, 11.24; Cl, 16.70.

[{trans-Pt(NH$_3$)$_2$Cl}$_2$— —N$^4$-CBz-spermidine-N$^1$,N$^8$]Cl$_2$ (3). 0.25 mMol 1 is dissolved in 20 mL H$_2$O and is combined with 0.75 mMol benzylchloroformate in 10 mL dioxane at 0° C. The mixture is allowed to come to room temperature and subsequently brought to pH 10 by means of 1 M NaOH. The clear solution is stirred for 24 h, the pH is periodically controlled and if necessary readjusted to 10-11. A small amount of a black precipitate is filtered off and the filtrate is concentrated to dryness. The solid is dissolved in 60 mL of boiling methanol and the solution is filtered to remove the insoluble starting compound. The methanolic solution is concentrated to ca 20 mL and a 3-5 fold excess of LiCl in methanol is added. The mixture is allowed to crystallize at 4° C. over night yielding 81% colorless crude product, which is recrystallized from water or methanol. The final yield is 70-75%. Anal. Calcd for $Cl_5H_{37}N_7O_2Cl_4Pt_2$: C, 20.49; H, 4.24; N, 11.15; Cl, 16.12. Found: C, 20.54; H, 4.28; N, 10.92; Cl, 16.15.

[{trans-Pt(NH$_3$)$_2$Cl}$_2$——N$^4$-Fmoc-spermidine-N$^1$,N$^8$]Cl$_2$ (4). A solution of 0.4 mMol 1 in 25 mL H$_2$O is adjusted to pH 9-10 with 2 M NaOH. 0.5 mMol fluorenylmethylchloroformate in 15 mL dioxane is added with stirring at 0° C., then the solution is allowed to come to room temperature. The pH is readjusted to 9-10 and the mixture is stirred at ambient temperature for 4 h. The solution is concentrated in vacuum to approximately 5 mL volume and then cooled to 4° C. A colorless precipitate is collected by from water and subsequently from methanol giving 4 in 58% yield. Anal. Calcd for $C_{22}H_{41}N_7O_2Cl_4Pt_2$: C, 27.31; H, 4.27; N, 10.13; Cl, 14.66. Found: C, 27.49; H, 4.36; N, 10.61; Cl, 14.95.filtration and washed with dioxane and diethylether. The crude product is recrystallized

Example 3

Hydrolysis Studies of Compounds 2-4

The hydrolysis of the protective groups of compounds 2-4 was monitored at 37° C. at various pH values. By the start of the reaction the HPLC chromatograms of all samples displayed only signals of the protected species. In addition, the chromatogram of 2 contained a peak of a minor impurity (ca 0.4%) which remained unchanged during the timecourse of the reaction. Deprotection of the secondary amino function leads to the appearance of a signal for the unprotected spermidine complex 1 that, as a consequence of the increased cationic charge, is well separated from the signal of the N4 blocked precursor. The area percentage of the integrated signal of the unprotected species is taken as an estimate for the amount of hydrolysis at a given timepoint. To allow for a more accurate quantitative comparison of results, the extinction coefficients for compounds 1-4 were determined at 215 nm (Table 1). The integral values of the blocked compounds have been corrected for the higher absorbance of these species at the observed wavelength compared to the unprotected species 1. Table 2 provides a summary of the amount of hydrolysis for all samples before and after the correction. Rate constants were calculated based on the corrected integral values.

Figure 7A:
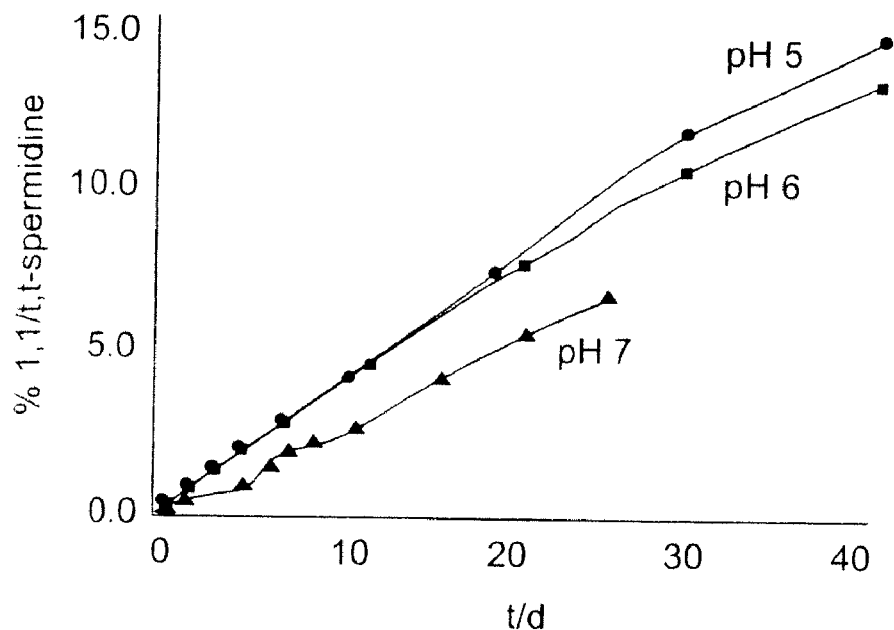
FIGS. 7A and 7B. Percentage of unprotected 1,1/tt-spermidine (1) found in the HPLC chromatograms of compounds 2 (A) and 4 (B), respectively, over time at different pH values.

The hydrolysis profile of compound 2 in the pH range between 5 and 7 is depicted in FIG. 7A. Although the BOC protecting group is regarded as stable in neutral and moderately acidic aqueous solutions, (14) a slow release over a time period of several days is evident from the data. After 25 days at neutral pH the signal of the unprotected Pt spermidine complex contributes with approximately 6% to the overall integration of the chromatogram. At lower pH values more hydrolysis product is detected, but the rate of cleavage is still low throughout the examined pH range. Approximately 13% of the free spermidine compound, 1, is released within 42 day at pH 6 compared to little more than 14% at pH 5. Rapid and complete acidic hydrolysis of the BOC group is known to take place at pH<2 and is commonly used for the deprotection of the amino function in tert-butylcarbamates (14). Benzylcarbamates show in general higher stability towards acidic hydrolysis and are usually removed by catalytic hydrogenolysis rather than by acid or base catalyzed cleavage (14). Therefore, it is not surprising that no significant amounts of spontaneous deprotection is evident from the HPLC profile of 3 at pH 5 and 6. Over the complete timecourse, the amount of 1 detected in the samples is well below 0.1%.

Figure 7B:
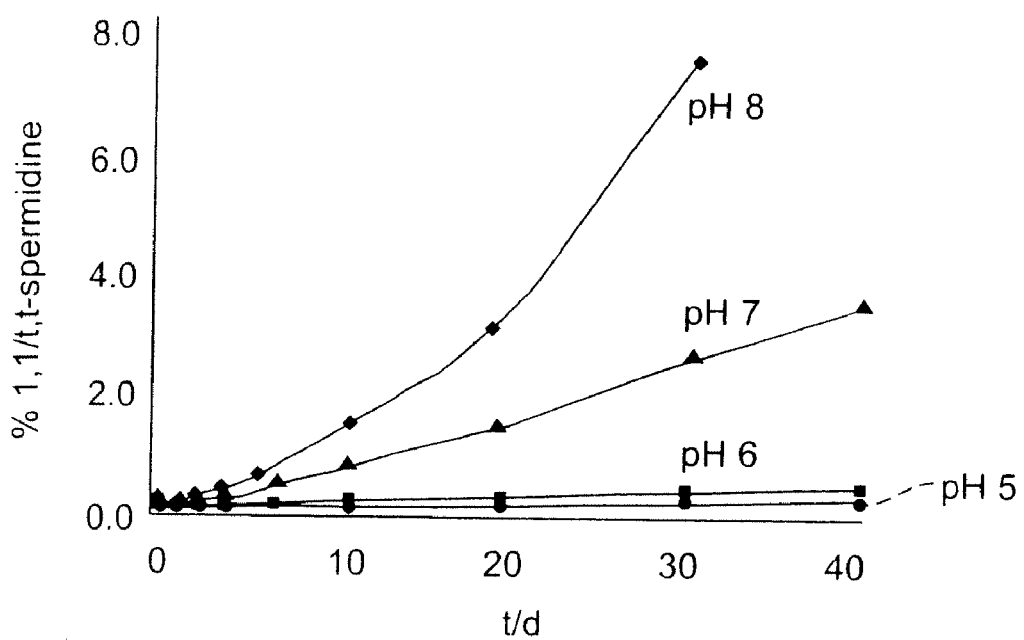

The HPLC profile of compound 4 at pH 5-8 is displayed in FIG. 7B. Similar to 3, only minor amounts of hydrolyzed species are observed at pH 5 and 6, proving the excellent acid stability of the Fmoc protection group. However, a steady increase in concentration of the unprotected complex is detected, meaning that slow decomposition of the carbamate is taking place under these conditions. Higher pH values strongly favor the deprotection of the complex and considerable amounts of free spermidine complex are released at pH 7 and 8. The reason for the reversed pH dependence of the hydrolysis reaction compared to complex 2 lies in the structure of the flourenylmethyl residue. The aromatic rings stabilize a dibenzocyclodienylanion, and therefore the reaction is believed to commence via a β elimination process, (15), allowing cleavage of fluorenylmethylcarbamates under mild basic conditions.

TABLE 1

Extinction coefficients of 1-4 at 215 nm and correction factors to account for different absorption of the compounds at this wavelength.

|   | $\epsilon_{215}/10^3$ | Correction Factor $\epsilon_{215}(1)/\epsilon_{215}$ |
| --- | --- | --- |
| 1 | 3.64 | 1 |
| 2 | 3.90 | 1.07 |
| 3 | 8.69 | 2.39 |
| 4 | 25.0 | 6.87 |

TABLE 2

Percentage of deprotected species 1 found in the samples of compounds 2-4 at various pH values. values in square brackets are corrected for the different extinction coefficients at 215 nm.

| | 2 | | 3 | | 4 | |
| --- | --- | --- | --- | --- | --- | --- |
| pH | % 1[a] | time [d][b] | % 1 | time [d] | % 1 | time [d] |
| 5 | 14.3 [15.1] | 42 | 0.05 [0.13] | 30 | 0.14 [1.0] | 41 |
| 6 | 13.0 [13.8] | 42 | 0.05 [0.12] | 42 | 0.45 [3.0] | 41 |
| 7 | 6.2 [6.6] | 25 | — | — | 3.4 [19.6] | 41 |
| 8 | — | — | — | — | 7.3 [35.2] | 30 |

[a]percentage of 1 of the overall integration in the chromatogram after incubation;
[b]time of incubation at 37° C.

In the range between pH 5 and 6 compound 2 clearly shows the highest hydrolysis rate in this series. However, at physiological pH the Fmoc complex 4 obviously undergoes faster deprotection than 2. Although no data were obtained for 3 at this pH, it is a reasonable assumption that the benzylcarbamate will become more stable with increasing pH (14). First order rate constants were calculated for the deprotection of compounds 4 and 2 (Table 3). No attempts were made to calculate rate constants for complex 3.

Example 4

Synthesis and Characterization of Compounds 5-7

Besides carbamates, the preparation of amides is the most common approach for the protection of the amino function and their synthesis and hydrolysis behavior is well described in the literature (14). For the amide series, a novel synthetic pathway in a water free solvent was developed. In order to facilitate reactions in organic solvents compound 1 had to be converted into the acetate derivatives 1a-c, FIG. 6, which posses reasonable solubility in methanol, acetonitrile and water. The intermediates 1a-c were subsequently reacted with the protecting agents (acid anhydrides). Acetic acid anhydride did not require addition of base, while the anhydrides of chloroacetic acid and trifluoroacetic acid gave significantly higher yields in the presence of triethylamine. In the final step of the synthesis the Pt—Cl bond is restored by reaction with NaCl in aqueous solution.

All compounds were analyzed by HPLC and NMR.

Preparations [{trans-Pt(NH$_3$)$_2$X}$_2$-μ-spermidine-N$^1$,N$^8$]X$_3$ (X=CH$_3$COO$^-$ (1a), CH$_2$ClCOO$^-$ (1b), CF$_3$COO$^-$ (1c)). 1.0 mMol of 1 was dissolved in 50 mL of water and 4.97 mMol of AgX were added with stirring. Stirring was continued for 24 hours at 40° C. in the dark. The mixture was then allowed to come to room temperature and was filtered through Celite. The filtrate was evaporated to dryness, giving a grey residue of 1b and 1c, respectively, which was redissolved in a minimum amount of water, filtered and brought to dryness. 1a was obtained as an oil, which crystallized upon stirring in 40 mL of acetone/diethylether (1:1). The yields for compounds 1a-c were quantitative.

1a: Anal. Calcd for C$_{17}$H$_{47}$N$_7$O$_{10}$Pt$_2$.2H$_2$O: C, 21.82; H, 5.49; N, 10.48. Found: C, 21.86; H, 5.16; N, 10.57. $^1$H NMR: δ 1.75 (m, 4H); 1.96/1.98 (s each, 15H); 2.11 (m, 2H); 2.70 (m, 4H); 3.10 (m, 4H).

1b: Anal. Calcd for C$_{17}$H$_{42}$N$_7$O$_{10}$Cl$_5$Pt$_2$: C, 19.05; H, 3.95; N, 9.15; Cl, 16.54. Found: C, 18.93; H, 3.78; N, 8.85; Cl, 16.41. $^1$H NMR: δ 1.76 (m, 4H); 2.10 (m, 2H); 2.71 (m, 4H); 3.11 (m, 4H); 4.06 (s, 6H); 4.14 (s, 4H).

1c: Anal. Calcd for C$_{17}$H$_{32}$N$_7$O$_{10}$F$_{15}$Pt$_2$.H$_2$O: C, 17.19; H, 2.89; N, 8.26. Found: C, 17.17; H, 2.71; N, 8.17. $^1$H NMR: δ 1.76 (m, 4H); 2.10 (m, 2H); 2.70 (m, 4H); 3.09 (m, 4H). $^{195}$Pt NMR: δ −2132 ppm.

[{trans-Pt(NH$_3$)$_2$Cl}$_2$-μ-N$^4$—CH$_3$CO-spermidine-N$^1$,N$^8$] Cl$_2$ (5). 0.5 mMol 1a and 4.4 mMol acetic anhydride were combined in 10 mL of methanol and stirred for 2 hours at ambient temperature. 30 mL water were added and the solution was washed with 3×30 mL diethylether. The aqueous solution was then brought to dryness, and the remaining oil was dissolved in 10 mL water. 2.0 mMol NaCl were added and the pH of the solution was adjusted to 3.8 with 0.5 M HCl. The mixture was stirred for 4 hours at room temperature and evaporated to dryness. The residue was recrystallized from methanol and subsequently from ethanol/water (4:1), the final yield being 54%. Anal. Calcd for C$_9$H$_{33}$N$_7$OCl$_4$Pt$_2$: C, 13.73; H, 4.22; N, 12.45; Cl, 18.01. Found: C, 13.70; H, 4.01; N, 12.17; Cl, 17.74. $^1$H NMR: δ 1.72 (m, 4H); 2.16 (s, 3H); 1.92/2.05 (m each, 2H); 2.74 (m, 4H); 3.40 (m, 2H); 3.47 (m, 2H). IR:ν$_{co}$ 1611 cm$^{-1}$.

[{trans-Pt(NH$_3$)$_2$Cl}$_2$-μ-N$^4$—CH$_2$ClCO-spermidine-N$^1$,N$^8$] (ClO$_4$)$_2$ (6). 0.5 mMol of 1b were suspended in 50 mL acetonitrile and 1.0 mMol triethylamine was added with stirring. The suspension was stirred at 40° C. and 20 mMol chloroacetic anhydride were added in several portions. After 24 hours all undissolved solid is filtered off (unprotected starting compound according to $^1$H NMR, ca 100 mg) and the filtrate was concentrated to dryness. The residue was dissolved in 25 mL water and washed with 2×20 mL diethylether. 2.5 mMol NaCl were added and the aqueous solution was stirred at ambient temperature for 2 hours. The solvent was removed in vacuum and the residue was redissolved in 60 mL methanol.

Undissolved solid was filtered off and the filtrate was concentrated to a small volume (<5 mL). Addition of 40 mL acetone/diethylether (1:1) caused the product to precipitate. Several recrystallizations from water, water/ethanol and water/DMF did not yield a pure product (purity<90% by HPLC). The product was HPLC purified with a semi preparative column (Waters Bondapak C18, 7.8 mm 300 mm), using a gradient elution method (solvent A: $H_2O$, 0.025 M $NaClO_4$; solvent B: $H_2O$, methanol (70:30), 0.025 M $NaClO_4$). The product was obtained as a perchlorate salt and was 99% pure by HPLC, with the final yield being 29%. Anal. Calcd for $C_9H_{32}N_7O_9Cl_5Pt_2$: C, 11.38; H, 3.40; N, 10.32. Found: C, 11.55; H, 3.08; N, 10.29. $^1$H NMR: δ 1.74 (m, 4H), 4.41/4.38 (s each, 2H); 1.93/2.09 (m each, 2H); 2.73 (m, 4H); 3.44 (m, 2H); 3.54 (m, 2H). IR: $ν_{CO}$ 1642 $cm^{-1}$.

[{trans-Pt($NH_3$)$_2$Cl}$_2$-μ-$N^4$—$CF_3$CO-spermidine-$N^1$,$N^8$] $Cl_2$ (7). 0.5 mMol of Ic were suspended in 40 mL acetonitrile and 1.0 mMol triethylamine was added to reach a clear solution. 30 mMol trifluoroacetic anhydride were added in several portions and the mixture was stirred for 24 hours at 40° C. The solvent was removed in vacuum and 20 mL acetone and 80 mL diethylether were added to the remaining oil. A white solid was filtered and washed with diethylether. The solid was dissolved in 20 mL water and stirred with 2.5 mMol NaCl for 2 hours (pH 2.4 with 0.5 M HCl). The solution was brought to dryness and the remaining residue is stirred in 200 mL methanol. The solution was filtered from some undissolved solid and evaporated in vacuum. The product was recrystallized from water, the yield was 61%. Anal. Calcd for $C_9H_{30}N_7OCl_4F_3Pt_2$: C, 12.85; H, 3.59; N, 11.65; Cl 16.86. Found: C, 12.68; H, 3.46; N, 11.20; Cl, 17.08. $^1$H NMR: δ 1.74 (m, 4H); 2.01/2.10 (m each, 2H); 2.73 (m, 4H); 3.53 (m, 2H); 3.59 (m, 2H). $^{195}$Pt NMR: δ −2415 ppm. IR: $ν_{CO}$ 1684 $cm^{-1}$.

Example 5

Hydrolysis Studies of Compounds 5-7

The hydrolysis of the blocking groups of on the N4 position of compounds 5-7 was monitored at 37° C. over a pH range of 6-8. By the start of the reaction the HPLC chromatograms of all samples displayed only signals of the protected species, together with minor impurities (<3% of the overall integration in all cases), but no 1,1/t,t-spermidine (3d, FIG. 3). The HPLC chromatograms of 5, the acetyl protected spermidine complex, did not show any changes over a time period of 35 days, indicating the excellent stability of the acetyl group in the observed pH range.

Figure 8:
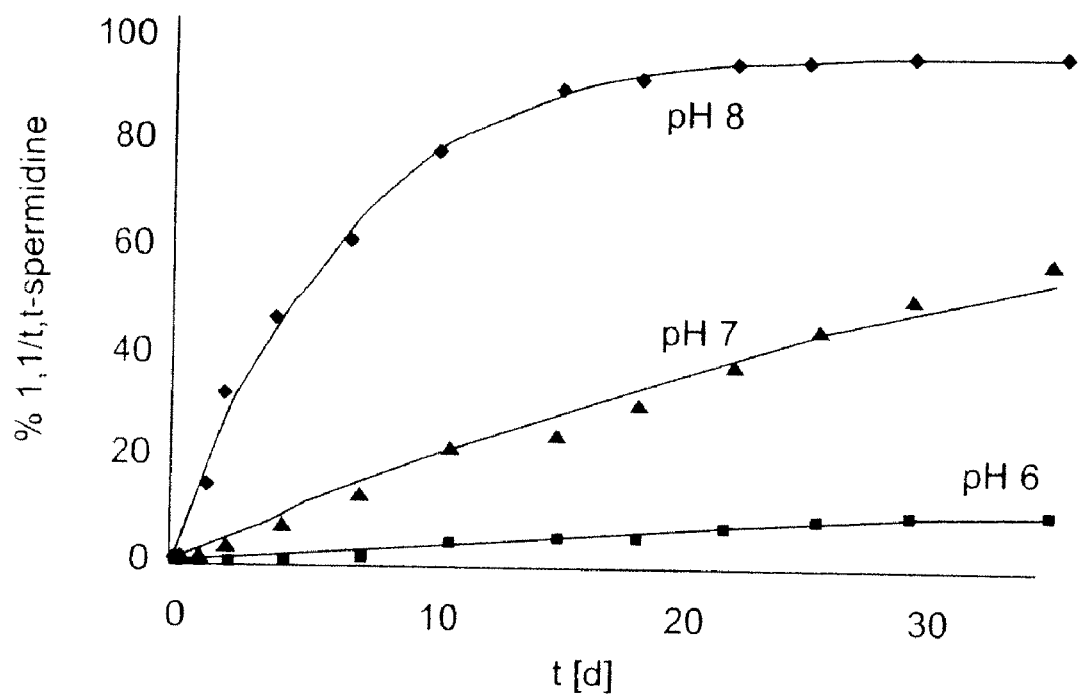
FIG. 8. Percentage of 1,1/tt-spermidine (1) found in the HPLC chromatograms of compound 7 at pH 6-8 over a timecourse of 35 days. The lines show the Scientist fit for a first order reaction.

Trifluoroacetyls are generally cleaved under mild conditions, (14) and the HPLC profile of compound 7 shows indeed the conversion of the N4 blocked species into the unprotected, protonated form, which is clearly separated in the chromatograms due to its increased cationic charge. The amount of 1,1/t,t-spermidine released over time is depicted in FIG. 8. No other products were detected, trifluoroacetate, originating from the hydrolysis reaction, is not retained on the column under the present conditions and coelutes with the other anions ($Cl^-$ from 5, $NO_3^-$ from pH adjustment). In order to obtain rate constants for the conversion of 7 to 1,1/t,t-spermidine, the integral values of the chromatograms were corrected for the different absorption of the species at the observed wavelength ($ε_{215}$: 1, 3.64·10$^3$; 5, 7.62·10$^3$; 6, 10.4·10$^3$; 7, 9.46·10$^3$ L.Mol$^{-1}$·cm$^{-1}$). Concentrations were calculated based on the assumption that the sum of the concentrations of both species at every time point equals the original concentration of 7 at the start of the experiment. First order rate constants were obtained using the program MicroMath Scientist Version 2.01. The results are summarized in Table 3 and compared with values obtained for BOC and Fmoc protected spermidine complexes.

TABLE 3

Rate Constants [$s^{-1}$] for the Deprotection of N4 Blocked Platinum Spermidine Complexes

| pH | Complex 7 | Complex 2 | Complex 4 |
|---|---|---|---|
| 8 | 1.79 (±0.03) · 10$^{-6}$ | — | 1.44 (±0.07) · 10$^{-7}$ |
| 7 | 2.73 (±0.06) · 10$^{-7}$ | 3.12 (±0.04) · 10$^{-8}$ | 6.12 (±0.09) · 10$^{-8}$ |
| 6.6 | — | 3.51 (±0.05) · 10$^{-8}$ | — |
| 6 | 4.44 (±0.11) · 10$^{-8}$ | 4.29 (±0.05) · 10$^{-8}$ | 9.74 (±0.88) · 10$^{-9}$ |
| 5 | — | 4.65 (±0.04) · 10$^{-8}$ | 3.99 (±0.96) · 10$^{-9}$ |

At neutral pH the hydrolysis rates for the protected spermidines of the amide and carbamate series follow the order 7>4>2>>5≈3 (for 6 see below). Decrease in pH by 1 unit leads to a reduction of the rate constants for 7 and 3 by almost one order of magnitude in the observed range, while 2 actually shows a moderate increase in its hydrolysis rate with lower pH. At pH 6, the rate constants follow the order 7≈2>4. Many solid tumors are known to accumulate lactic acid, resulting in a reduced intracellular pH value (17). Therefore, the prodrugs most suited for targeting those tumor cells might be the ones that show increased release of the active species under slightly acidic conditions.

Example 6

Biological Activity of Compounds 2-7

Figure 1:
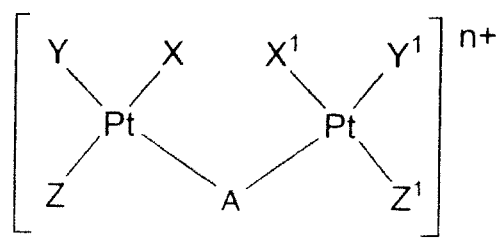
FIG. 1 shows the generic structure of diamine or polyamine-bridged dinuclear platinum complexes.

To examine the pro-drug potential in a biological setting, a comparison of the pharmacological properties of the blocked polyamine compounds in L1210 murine leukemia cells was undertaken. The results are presented in Table 4. As can be seen, the BOC-spermidine compound 2 showed intermediate potency between that of a standard 2+ compound, 1,1/t,t (n=6) (FIG. 1a), and the "parent" 1,1/t,t-spermidine 1 carrying a 3+ charge. Incorporation of charge and hydrogen-bonding capability into the linking diamine or polyamine has been shown to dramatically enhance cellular accumulation in polynuclear platinum complexes (7, 16). The cellular uptake of the 1,1/t,t-spermidine compound (overall charge is 3+) is known to be high and significantly enhanced over "simple" dinuclear compounds such as [trans-{PtCl($NH_3$)$_2$}$_2$$H_2$N($CH_2$)$_6$$NH_2$]$^{2+}$ (overall charge is 2+) (16).

The cellular accumulation of the blocked Pt compound 2 was also investigated. Interestingly, cellular accumulation of the BOC-spermidine compound in the L1210/DDP (the subline resistant to cisplatin) was intermediate between that observed for the 1,1/t,t (n=6) 2+ and spermidine 3+ compounds. Based solely on charge considerations the BOC-spermidine with a charge of 2+ should have cellular uptake similar to 1,1/t,t (n=6). The enhanced uptake could be explained by some hydrolysis in media or plasma producing small amounts of the protonated 1,1/t,t-spermidine. Considering the potency of polynuclear-polyamine compounds, a small percentage of hydrolysis could have a significant impact on in vivo activity. This experiment demonstrates that the enhanced uptake of 2 over the, 1,1/t,t n=6 derivative could be due to some production of the hydrolysed species in tissue culture with therefore some contribution to overall uptake coming from 1.

TABLE 4

Growth inhibition and accumulation of Pt complexes in L1210 cell lines after 2 hours of exposure.

| Platinum complex | Growth Inhibition | | | Accumulation[b] | |
|---|---|---|---|---|---|
| | L1210/0 | L1210/DDP | RF[c] | L1210/0 | L1210/DDP |
| cisplatin | 1.3 (0.37) | 59 (6.0) | 44 | 5.0 (0.89) | 1.5 (0.76 |
| 1 | 0.75 (0.29) | 0.26 (0.232) | 0.35 | 17 (3.4) | 20 (2.1) |
| 2 | 1.25 (0.13) | 4.6 (1.0) | 3.7 | 5.0 (0.63) | 4.8 (0.75) |
| 1,1/tt | 3.7 (0.37) | 16 (2.8) | 4.3 | 3.8 (0.70) | 0.67 (0.21) |

[a]$IC_{50}$ (μM) mean (±SE) for 3 experiments of 2 determinations each;
[b]attamol Pt complex/cell (±SE) for 3 experiments of 2 determinations each;
[c]resistance factor, [($IC_{50}$ L1210/platinum complex)/$IC_{50}$ L1210/0)]. See reference 7 for details.

In a panel of human ovarian cancer cell lines, the blocked polyamine compounds showed different patterns of cytotoxicity amongst themselves and also in comparison to the "free" polyamine compound, Table 5. Of special interest is the remarkably low value for 4 (Fmoc) in A2780 cells.

TABLE 5

96H $IC_{50}$ (μM) values in human ovarian carcinoma cell lines sensitive and resistant to cisplatin.[a]

| | Cell line | | | | | |
|---|---|---|---|---|---|---|
| Complex | A2780 | A2780/ CDDP (RF)[a] | CH1 | CH1/ CDDP (RF) | 41M | CH1/ CDDP (RF) |
| cisplatin | 1.6 | 12.0 (7.5) | 0.34 | 1.1 (3.2) | 2.3 | |
| 1 | <0.25 | <0.25 | 0.43 | 0.35 (0.8) | <0.25 | |
| 2 | 2.1 | 19.0 (9.0) | 8.0 | 11.0 (1.4) | 17.0 | |
| 3 | 24.0 | 100.0 (4.2) | 25.0 | 43.0 (1.7) | >100 | |
| 4 | 0.84 | 65.0 (77) | 46.0 | 62.0 (1.3) | >100 | |
| 5 | 14.0 | 54.0 (3.9) | 7.4 | 12.5 (1.7) | 17.5 | 24.0 (1.4) |
| 7 | 6.8 | 46.0 (6.8) | 2.4 | 5.0 (2.1) | 3.7 | 19.0 (5.1) |

[a]Resistance factor, RF = $IC_{50}$ resistant/$IC_{50}$ parent line.

These results suggest that the activity of the blocked polyamine-platinum compounds may be cell line specific, opening the possibility for drug development in selected tumors or drug delivery. Further, by altering the nature of the blocking group, the release of the active species can be tailored for a specific locality or purpose. For example, the stability of the Fmoc complex at pH 5 and 6 could allow for oral delivery, stabilizing the compound to the acid of the stomach but releasing the active species at pH 7-8.

While the invention has been described in terms of its preferred embodiments, those skilled in the art will recognize that the invention can be practiced with modification within the sprit and scope of the appended claims. Accordingly, the present invention should not be limited to the embodiments as described above, but should further include all modifications and equivalents thereof within the spirit and scope of the description provided herein.

REFERENCES 1. (a) Farrell, N. in *Platinum-Based Drugs in Cancer Therapy;* Kelland, L. R.; Farrell, N. Eds.; Humana Press, 2000, pp 321-338. (b) Farrell, N.; Qu, Y.; Bierbach, U.; Valsecchi, M.; Menta, E. in 30 *Years of Cisplatin - Chemistry and Biochemistry of a Leading Anticancer Drug;* Lippert, B. Ed.; Verlag, 1999, pp 479-496. (c) Farrell, N.; Spinelli, S. in *Uses of Inorganic Chemistry in Medicine;* Farrell, N. Ed.; Royal Society of Chemistry, 1999, pp 124-134.
2. Qu, Y.; Rauter, H.; Soares Fontes, A. P.; Bandarage, R.; Kelland, L. R.; Farrell, N. *J. Med. Chem.* 2000, 43, 3189-3192
3. Calvert, P. M. H.; Hughes, A. N.; Plummer, E. R.; Azzabi, A. S. T.; Verrill, M. W.; Camboni, M. G.; Verdi, E.; Berareggi, A.; Zuchetti, M.; Robinson, A. M.; Carmichael, J.; Calvert, A. H. *Clinical Cancer Research* 1999, 5, 3796.
4. McGregor, T. D.; Kasparkova, J.; Neplechova, K.; Novakova, O.; Penazova, H.; Vrana, O.; Brabec, V.; Farrell, N. *J. Biol Inorg. Chem.* 2002, 7, 397.
5. Rauter, H.; DiDomenico, R.; Menta, E.; Da Re, G.; De Cillis, G.; Conti, M.; Lotto, A.; Pavesi, P.; Spinelli, S.; Manzotti, C.; Piazzoni, L.; Farrell, N. *Proc. AACR* 1998, 39, 1096.
6. Rauter, H.; DiDomenico, R.; Menta, E.; Oliva, A.; Qu, Y.; Farrell, N. *Inorg. Chem.* 1997, 36, 3919.
7. Roberts, J. D.; Peroutka, J.; Farrell, N. *J Inorg. Biochem.* 1999, 77, 51-57.
8. Kelland, L. R.; Jones, M.; Abel, G.; Valenti, M.; Gwynne, J.; Karrap, K. R. *Cancer Chemotherapy and Pharmacology* 1992, 30, 43-50.
9. Kelland, L. R.; Barnard, C. F. J.; Mellish, K. J.; Jones, M.; Goddard, P. M.; Valenti, M.; Bryant, A.; Murrer, B. A.; Harrap, K. R. *Cancer Research* 1994, 54, 5618-5622.
10. Skehan, P.; Storeng, R.; Scudiero, D.; Monks, A.; Mcmahon, J.; Visitica, D.; Warren, J.; Bokesch, H.; Kennedy, S.; Boyd, M. R. *Journal of the National Cancer Institute* 1990, 82, 1107-1112.
11. Tribolet, R.; Sigel, H. *Eur. J Biochem.* 1987, 163, 353.
12. Martin, R. B. *Science* 1963, 139, 1198.
13. Smith, J. W. in *Chemistry of the Amino Group*; S. Patai Ed.; Interscience Publishers, London/New York, 1968.
14. Greene, T. W.;. Wuts, P. G. M *Protective Groups in Organic Synthesis;* John Wiley & Sons, 3rd edition, 1999.
15. Carpino, L. A.; Han, G. Y. *J. Org. Chem.* 1972, 37, 3404.
16. Roberts, J. D.; Peroutka, J.; Beggiolin, G.; Manzotti, C.; Piazzoni, L.; Farrell, N. *J. Inorg. Biochem.* 1999, 77, 47-50.
17. Gerweck, L. E. *Semin. Radiat. Oncol.* 1998, 8, 176-182.

We claim:

1. A linear polyamine-bridged platinum compound having the general formula

[(PtXYZ)-A-(Pt X'Y'Z')], or salts thereof, where X, Y, Z, X', Y', and Z' may be the same or different and are
anionic groups, or
neutral groups which may be substituted or unsubstituted; and
A is a bridging polyamine having a general formula selected from the group consisting of
$H_2N(CH_2)_xNBB'(CH_2)_yNH_2$ where x ranges from 1 to 10 and y ranges from 1 to 10, or
$H_2N(CH_2)_xNBB'(CH_2)_yNBB'(CH_2)_xNH_2$ where x ranges from 1 to 10 and y ranges from 1 to 10,
where B and B' are hydrogen or a labile blocking group and may be the same or different, and may be the same or different at each location, and where B' may be present or absent,
and wherein when said anionic groups or neutral groups of said linear polyamine-bridged platinum compound are in a 1,1/t,t configuration with respect to said bridging polyamine, said labile blocking group is not tBOC;
and wherein
i) said anionic groups are selected from the group consisting of halide, pseudohalide, substituted pseudohalide, sulphate, phosphate, phosphonate, nitrate, carboxylate, substituted carboxylate, dicarboxylate, and substituted dicarboxylate;
ii) said neutral groups are selected from the group consisting of ammonia, primary or secondary amines, a "dangling" diamine $H_2N(CH_2)_nNBB'$ where only the $-NH_2$ moiety is bound to platinum, pyridine, substituted pyridine, quinoline, imidazole, thiazole, pyrimidine, purine, acridine, pyrazole, benzimidazole, and benzothiazole; and for 1,1/c,c configurations, Y, Y', Z and Z' may be a chelating bidentate diamine; and
iii) said labile blocking group is an amide protection group,
with the proviso that when x =4, y =3, and at least two of X, Y, Z and X', Y', Z' are $NH_3$, one of B or B' is a labile protecting group.

2. The compound of claim 1 wherein said bridging polyamine portion of said compound is $H_2N(CH_2)_xNBB'(CH_2)_yNH_2$ and x ranges from 1 to 10 and y ranges from 1 to 10.

3. The compound of claim 2 wherein the values of x and y are selected from the group consisting of: x=4 and y=3, x=6 and y=6; and x=7 and y=8.

4. The compound of claim 3 wherein
Y=Y' and is chloride; and
X=X' and Z=Z' and are ammonia.

5. The compound of claim 3 wherein
X=X' and is chloride; and
Y=Y' and Z=Z' and are ammonia or a cheating bidentate diamine.

6. The compound of claim 1 wherein said bridging polyamine portion of said compound is $H_2N(CH_2)_xNBB'(CH_2)_yNBB'(CH_2)_xNH_2$ and x ranges from 1 to 10 and y ranges from 1 to 10.

7. The compound of claim 6 wherein the values of x and y are selected from the group consisting of: x=4 and y=3; x=6 and y=2; and x=5 and y=4.

8. The compound of claim 7 wherein
Y=Y' and is chloride; and
X=X' and Z=Z' and are ammonia.

9. The compound of claim 1 wherein said amide protection group is selected from the group consisting of 2-(benzoyloxymethyl)benzoyl (BOMB), acetyl, trifluoroacetyl, and monochloroacetyl.

10. The compound of claim 1 wherein said blocking group further comprises a targeting element.

11. The compound of claim 1 wherein said anionic groups are arranged in a 1,1/t,t configuration with respect to said bridging polyamine.

12. The compound of claim 1 wherein said anionic groups are arranged in a 1,1/c,c configuration with respect to said bridging polyamine.

13. The compound of claim 1 wherein said anionic groups or neutral groups are arranged in a 2,2/c,c configuration with respect to said bridging polyamine.

14. A method for killing cancer cells, comprising the steps of
providing to said cancer cells a linear polyamine-bridged platinum compound having the general formula [(PtXYZ)-A-(Pt X'Y'Z')], or salts thereof, where X, Y, Z, X', Y', and Z' may be the same or different and are
anionic groups, or
neutral groups which may be substituted or unsubstituted; and
A is a bridging polyamine having a general formula selected from the group consisting of
$H_2N(CH_2)_xNH_2(CH_2)_yNH_2$ where x ranges from 1 to 10 and y ranges from 1 to 10, or
$H_2N(CH_2)_xNBB'(CH_2)_yNBB'(CH_2)_xNH_2$ where x ranges from 1 to 10 and y ranges from 1 to 10;
where B and B' are hydrogen or a labile blocking group and may be the same or different, and may be the same or different at each location, and where B' may be present or absent,
and wherein at least one central amine function of said bridging polyamine portion is blocked with a labile blocking group,
wherein said linear polyamine-bridged platinum compound is provided in a quantity sufficient to kill said cancer cells;
and wherein
i) said anionic groups are selected from the group consisting of halide, pseudohalide, substituted pseudohalide, sulphate, phosphate, phosphonate, nitrate, carboxylate, substituted carboxylate, dicarboxylate, and substituted dicarboxylate;
ii) said neutral groups are selected from the group consisting of ammonia, primary or secondary amines, a "dangling" diamine $H_2N(CH_2)_nNBB'$ where only the $-NH_2$ moiety is bound to platinum, pyridine, substituted pyridine, quinoline, imidazole, thiazole, pyrimidine, purine, acridine, pyrazole, benzimidazole, and benzothiazole; and for 1,1/c,c configurations, Y, Y', Z and Z' may be a chelating bidentate diamine; and
iii) said labile blocking group is an amide protection group,
with the proviso that when x =4, y =3, and at least two of X, Y, Z and X', Y', Z' are $NH_3$, one of B or B' is a labile protecting group.

15. The method of claim 14 wherein said bridging polyamine portion of said compound is $H_2N(CH_2)_xNBB'(CH_2)_yNH_2$ and x ranges from 1 to 10 and y ranges from 1 to 10.

16. The method of claim 15 wherein the values of x and y are selected from the group consisting of: x=4 and y=3, x=6 and y=6; and x=7 and y=8.

17. The method of claim 16 wherein
Y=Y' and is chloride; and
X=X' and Z=Z' and are ammonia.

18. The method of claim 16 wherein
X=X' and is chloride; and
Y=Y' and Z=Z' and are ammonia or a chelating bidentate diamine.

19. The method of claim 14 wherein said bridging polyamine portion of said compound is $H_2N(CH_2)_xNBB'(CH_2)_yNBB'(CH_2)_xNH_2$ and x ranges from 1 to 10 and y ranges from 1 to 10.

20. The method of claim 19 wherein the values of x and y are selected from the group consisting of: x=4 and y=3; x=6 and y=2; and x=5 and y=4.

21. The method of claim 20 wherein
Y=Y' and is chloride; and
X=X' and Z=Z' and are ammonia.

22. The method of claim 14 wherein said amide protection group is selected from the group consisting of 2-(benzoyloxymethyl)benzoyl (BOMB), acetyl, trifluoroacetyl, and monochloroacetyl.

23. The method of claim 14 wherein said labile blocking group further comprises a targeting element.

24. The method of claim 14 wherein said anionic groups or neutral groups are arranged in a 1,1/t,t configuration with respect to said bridging polyamine.

25. The method of claim 14 wherein said anionic groups or neutral groups are arranged in a 1,1/c,c configuration with respect to said bridging polyamine.

26. The method of claim 14 wherein said anionic groups or neutral groups are arranged in a 2,2/c,c configuration with respect to said bridging polyamine.

27. The method of claim 14 further comprising the step of removing said labile blocking group via an environmental stimulus.

28. The method of claim 27 wherein said environmental stimulus is selected from the group consisting of pH and an enzyme.

29. A linear polyamine-bridged platinum compound having the general formula [(PtXYZ)-A-(Pt X'Y'Z')], or salts thereof, where X, Y, Z, X', Y', and Z' may be the same or different and are
anionic groups, or
neutral groups which may be substituted or unsubstituted; and
A is a bridging polyamine having a general formula selected from the group consisting of
$H_2N(CH_2)_xNH_2(CH_2)_yNH_2$ where x ranges from 1 to 10 and y ranges from 1 to 10, or
$H_2N(CH_2)_xNBB'(CH_2)_yNBB'(CH_2)_xNH_2$ where x ranges from 1 to 10 and y ranges from 1 to 10;
where B and B' are hydrogen or a labile blocking group and may be the same or different, and may be the same or different at each location, and where B' may be present or absent,
and wherein said anionic groups or neutral groups are arranged in a 1,1/c,c or a 2,2/c,c configuration with respect to said bridging polyamine;
and wherein
i) said anionic groups are selected from the group consisting of halide, pseudohalide, substituted pseudohalide, sulphate, phosphate, phosphonate, nitrate, carboxylate, substituted carboxylate, dicarboxylate, and substituted dicarboxylate; and
ii) said neutral groups are selected from the group consisting of ammonia, primary or secondary amines, a "dangling" diamine $H_2N(CH_2)_nNBB'$ where only the —$NH_2$ moiety is bound to platinum, pyridine, substituted pyridine, quinoline, imidazole, thiazole, pyrimidine, purine, acridine, pyrazole, benzimidazole, and benzothiazole; and for 1,1/c,c configurations, Y, Y', Z and Z' may be a chelating bidentate diamine; and
iii) said labile blocking group is an amide protection groups,
with the proviso that when x=4, y=3, and at least two of X, Y, Z and X', Y', Z' are $NH_3$, one of B or B' is a labile protecting group.

30. The compound of claim 29 wherein said bridging polyamine portion of said compound is $H_2N(CH_2)_xNBB'(CH_2)_yNH_2$ and x ranges from 1 to 10 and y ranges from 1 to 10.

31. The compound of claim 30 wherein the values of x and y are selected from the group consisting of: x=4 and y=3, x=6 and y=6; and x=7 and y=8.

32. The compound of claim 31 wherein
Y=Y' and is chloride; and
X=X' and Z=Z' and are ammonia.

33. The compound of claim 31 wherein
X=X' and is chloride; and
Y=Y' and Z=Z' and are ammonia or a chelating bidentate diamine.

34. The compound of claim 29 wherein said bridging polyamine portion of said compound is $H_2N(CH_2)_xNBB'(CH_2)_yNBB'(CH_2)_xNH_2$ and x ranges from 1 to 10 and y ranges from 1 to 10.

35. The compound of claim 34 wherein the values of x and y are selected from the group consisting of: x=4 and y=3; x=6 and y=2; and x=5 and y=4.

36. The compound of claim 35 wherein
Y=Y' and is chloride; and
X=X' and Z=Z' and are ammonia.

37. The compound of claim 29 wherein said carbamate protection groups are selected from the group consisting of t-butyl (tBOC), benzyl (CBz), fluorenylmethyl (Fmoc), adamantyl (1-Adoc), piperidinyl (Pipoc), allyl, and vinyl.

38. The compound of claim 29 wherein said amide protection groups are selected from the group consisting of 2-(benzoyloxymethyl)benzoyl (BOMB), acetyl, trifluoroacetyl, and monochloroacetyl.

39. The compound of claim 29 wherein said blocking group further comprises a targeting element.

40. A method of producing a linear platinum compound with a polyamine bridge in which amine groups of said polyamine bridge are blocked with an amide blocking group, comprising the steps of
substituting anionic leaving groups of said linear platinum compound with acetate to form an acetate derivative of said linear platinum compound;
blocking amine groups of said polyamine bridge by reacting said acetate derivative of said linear platinum compound with an acid anhydride of said amide blocking group under anhydrous conditions to form a blocked amide derivative of said linear platinum compound; and
forming a blocked anionic derivative of said linear platinum compound by exposing said blocked acetate derivative of said linear platinum compound to anions under conditions which result in the replacement of said acetate by said anions.

41. A method of producing a linear platinum compound with a polyamine bridge in which amine groups of said polyamine bridge are blocked with a carbamate blocking group, comprising the step of
reacting said linear platinum compound with a carbamate precursor in an alkaline dioxane/water system under conditions in which a blocked carbamate derivative of said linear platinum compound is formed.

42. A method for providing a linear polyamine-bridged platinum compound at a location of interest, comprising the steps of
  positioning a blocked linear polyamine-bridged platinum compound formed by attaching a labile blocking group to at least one central amine function of a bridging polyamine portion of said compound at said location of interest, and
  exposing said blocked linear polyamine-bridged platinum compound to an environmental stimulus which causes removal of said labile blocking group.

43. The method of claim 42 wherein said blocked linear polyamine-bridged platinum compound has the general formula [(PtXYZ)-A-(Pt X'Y'Z')], or salts thereof,
  where X, Y, Z, X', Y', and Z' may be the same or different and are
    anionic groups, or
    neutral groups which may be substituted or unsubstituted; and
  A is a bridging polyamine having a general formula selected from the group consisting of
    $H_2N(CH_2)_xNBB'(CH_2)_yNH_2$ where x ranges from 1 to 10 and y ranges from about 1 to 10, or
    $H_2N(CH_2)_xNBB'(CH_2)_yNBB'(CH_2)_xNH_2$ where x ranges from 1 to 10 and y ranges from about 1 to about 10,
  where B and B' are hydrogen or a labile blocking group and may be the same or different, and may be the same of different at each location within the compound, and where B' may be present or absent,
  and wherein at least one central amine of said bridging polyamine portion is blocked with a labile blocking group;
  and wherein
    i) said anionic groups are selected from the group consisting of halide, pseudohalide, substituted pseudohalide, sulphate, phosphate, phosphonate, nitrate, carboxylate, substituted carbxylate, dicarboxylaate, and substituted dicarboxylate;
    ii) said neutral groups are selected from the group consisting of ammonia, primary or secondary amines, a "dangling" $H_2N(CH_2)_nNBB'$ where only the-$NH_2$ moiety is bound to platinum, pyridine, substituted pyridine, quinoline, imidazole, thiazole, pyrimidine, purine, acridine, pyrazole benzimidazole, and benzothiazole; and for 1,1/c,c configurations, Y,Y', Z and Z' may be a chelating bidentata diamine; and
    iii) said labile blocking group is an amide protection group, with the proviso that when x =4, y =3, and at least two of X,Y,Z and X', Y', Z' are $NH_3$, one of B or B' is a labile protecting group.

44. The method of claim 43 wherein said bridging polyamine portion of said compound is $H_2N(CH_2)_xNBB'(CH_2)_yNH_2$ and x ranges from about 1 to10and y ranges from 1 to 10.

45. The method of claim 44 wherein the values of x and y are selected from the group consisting of: x=4 and y=3, x=6 and y=6; and x=7 and y=8.

46. The method of claim 45 wherein
  Y=Y' and is chloride; and
  X=X' and Z=Z' and are ammonia.

47. The method of claim 45 wherein
  X=X' and is chloride; and
  Y=Y' and Z=Z' and are ammonia or a chelating bidentate diamine.

48. The method of claim 43 wherein said bridging polyamine portion of said compound is $H_2N(CH_2)_xNBB'(CH_2)_yNBB'(CH_2)_xNH_2$ and x ranges from 1 to 10 and y ranges from 1 to 10.

49. The method of claim 48 wherein the values of x and y are selected from the group consisting of: x=4 and y=3; x=6 and y=2; and x=5 and y=4.

50. The method of claim 49 wherein
  Y=Y' and is chloride; and
  X=X' and Z=Z' and are ammonia.

51. The method of claim 43 wherein said amide protection groups are selected from the group consisting of 2-(benzoyloxymethyl)benzoyl (BOMB), acetyl, trifluoroacetyl, and monochloroacetyl.

52. The method of claim 42 wherein said blocking group further comprises a targeting element.

53. The method of claim 42 wherein said environmental stimulus is selected from the group consisting of pH and an enzyme.

54. The compound of claim 14, wherein said cancer cells are selected from the group consisting of ovarian cancer cells and prostate cancer cells.

55. The method of claim 54, wherein said can cancer cells are ovarian cancer cells.

56. The method of claim 14 wherein said linear polyamine-bridged platinum compound has the general formula [(PtXYZ)-A-(Pt X'Y'Z')], or salts thereof, where X, Y, Z, X', Y', and Z'may be the same or different and are
  anionic groups, or
  neutral groups which may be substituted or unsubstituted; and
  A is a bridging polyamine having a general formula selected from the group consisting of
    $H_2N(CH_2)_xNH_2(CH_2)_yNH_2$ where x ranges from 1 to 10 and y ranges from 1 to 10, or
    $H_2N(CH_2)_xNBB'(CH_2)_{y\ NBB'(CH2)}{}_xNH_2$ where x ranges from 1 to 10 and y ranges from 1 to 10;
  where B and B' are hydrogen or a labile blocking group and may be the same or different, and may be the same or different at each location, and where B' may be present or absent,
  and wherein said anionic groups or neutral groups are arranged in a 1,1/c,c or a 2,2/c,c configuration with respect to said bridging polyamine;
  and wherein
    i) said anionic groups are selected from the group consisting of halide, pseudohalide, substituted pseudohalide, sulphate, phosphate, phosphonate, nitrate, carboxylate, substituted carboxylate, dicarboxylate, and substituted dicarboxylate; and
    ii) said neutral groups are selected from the group consisting of ammonia, primary or secondary amines, a "dangling" diamine $H_2N(CH_2)_nNBB'$ where only the —$NH_2$ moiety is bound to platinum, pyridine, substituted pyridine, quinoline, imidazole, thiazole, pyrimidine, purine, acridine, pyrazole, benzimidazole, and benzothiazole; and for 1,1/c,c configurations, Y, Y', Z and Z' may be a chelating bidentate diamine; and
    iii) said labile blocking group is selected from the group consisting of carbamate protection groups and amide protection groups,
  with the proviso that when x =4, y =3, and at least two of X, Y, Z and X', Y', Z' are $NH_3$, one of B or B' is a labile protecting group.

57. The method of claim 42 wherein said linear polyamine-bridged platinum compound has the general formula

[(PtXYZ)-A-(Pt X"Y'Z')], or salts thereof, where X, Y, Z, X', Y', and Z' may be the same or different and are
  anionic groups, or
  neutral groups which may be substituted or unsubstituted; and
A is a bridging polyamine having a general formula selected from the group consisting of
  $H_2N(CH_2)_xNH_2(CH_2)_yNH_2$ where x ranges from 1 to 10 and y ranges from 1 to 10, or
  $H_2N(CH_2)_xNBB'(CH_2)_yNBB'(CH_2)_xNH_2$ where x ranges from 1 to 10 and y ranges From 1 to 10;
where B and B' are hydrogen or a labile blocking group and may be the same or different, and may be the same or different at each location, and where B' may be present or absent,
and wherein said anionic groups or neutral groups are arranged in a 1,1/c,c or a 2,2/c,c configuration with respect to said bridging polyamine;
and wherein
  i) said anionic groups are selected from the group consisting of halide, pseudohalide, substituted pseudohalide, sulphate, phosphate, phosphonate, nitrate, carboxylate, substituted carboxylate, dicarboxylate, and substituted dicarboxylate; and
  ii) said neutral groups are selected from the group consisting of ammonia, primary or secondary amines, a "dangling" diamine $H_2N(CH_2)_nNBB'$ where only the -$NH_2$ moiety is bound to platinum, pyridine, substituted pyridine, quinoline, imidazole, thiazole, pyrimidine, purine, acridine, pyrazole, benzimidazole, and benzothiazole; and for 1,1/c,c configurations, Y, Y', Z and Z, may be a chelating bidentate diamine; and
  iii) said labile blocking group is selected from the group consisting of carbamate protection groups and amide protection groups,
with the proviso that when x =4, y =3, and at least two of X, Y, Z and X', Y', Z' are $NH_3$, one of B or B' is a labile protecting group.

58. The linear polyamine-bridged platinum compound of claim 1, wherein said chelating bidentate diamine is selected from the group consisting of ethylenediamine, 1,2-diaminocyclohexane and 1,1'-diaminomethylcyclohexane.

59. The method of claim 14, wherein said chelating bidentate diamine is selected from the group consisting of ethylenediamine, 1,2-diaminocyclohexane and 1,1'-diaminomethylcyclohexane.

60. The linear polyamine-bridged platinum compound of claim 29, wherein said chelating bidentate diamine is selected from the group consisting of ethylenediamine, 1,2-diaminocyclohexane and 1,1'-diaminomethylcyclohexane.

61. The method of claim 43, wherein said chelating bidentate diamine is selected from the group consisting of ethylenediamine, 1,2-diaminocyclohexane and 1,1'-diaminomethylcyclohexane.

* * * * *